United States Patent
Allaway et al.

(10) Patent No.: US 6,261,763 B1
(45) Date of Patent: Jul. 17, 2001

(54) FLUORESCENCE RESONANCE ENERGY TRANSFER SCREENING ASSAY FOR THE IDENTIFICATION OF COMPOUNDS THAT ARE CAPABLE OF ABROGATING MACROPHAGE-TROPIC HIV-1 CELL FUSION

(75) Inventors: Graham P. Allaway, Moreton Merseyside (GB); Virginia M. Litwin, Fayetteville; Paul J. Maddon, Elmsford, both of NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 08/973,601

(22) PCT Filed: Jun. 7, 1996

(86) PCT No.: PCT/US96/09894

§ 371 Date: Mar. 16, 1998

§ 102(e) Date: Mar. 16, 1998

(87) PCT Pub. No.: WO96/41020

PCT Pub. Date: Dec. 19, 1996

Related U.S. Application Data

(63) Continuation-in-part of application No. 08/475,515, filed on Jun. 7, 1995.

(51) Int. Cl.[7] .................................................. C12Q 1/70
(52) U.S. Cl. ................. 435/5; 435/7.1; 435/7.2; 435/7.24
(58) Field of Search .................... 435/4, 5, 7.1, 7.2, 435/7.92, 172.3

(56) References Cited

PUBLICATIONS

Chams, et al., (1992) "Simple Assay To Screen for Inhibitors of Interaction Between the Human Immunodeficiency Virus Envelope Glycoprotein and Its Cellular Receptor, CD4" *Antimicrobial Agents and Chemotherapy* 36(2):262–272 (Exhibit 1).

Dimitrov. D.S., et al., (1991) "Initial Stages of HIV–1 Envelope Glycoprotein–Mediated Cell Fusion Monitored by a New Assay Based on Redistribution of Fluorescent Dyes" *AIDS Res. & Human Retroviruses* (7(10):799–805 (Exhibit 2).

Dragic, et al., (1993) "Different Requirement for membrane Fusion Mediated by the Envelopes of Human Immunodeficiency" *Journal of Virology* 67(2):2355–2359 (Exhibit 3).

Fouchier, et al., (1994) "HIV–1 Macrophage Tropism Is Determined at Multiple Levels of the Viral Replication Cycle" *Journal of Clinical Investigation* 94:1806–1814 (Exhibit 4).

Keller, P.M., et al., (1977) "A Fluorescence Enhancement Assay of Cell Fusion" *J. Cell Sci.* 28:167–177.

Mitsuya, H., et al., (1985) "Protection of T Cells Against Infectivity and Cytopathic Effect of HTLV–III In Vitro, in Miwa, et al. Eds., Retroviruses in Human Lymphoma Leukemia" *Japan Sci, Soc. Press, Tokyo/VNU Science Press*, Utrecht pp. 277–288.

Sandstrom, E.G. and Kaplan, J.C., (1987) "Antiviral Therapy in AIDS: Clinical Pharmacological Properties and Therapeutic Experience to Date" *Drugs* 34:372–390.

Wanda, P.E., and Smith, J.D., (1983) "A General Method for Heterokaryon Detection Using Resonance Energy Transfer and a Fluorescence–activated Cell Sorter" *J. Histochem. & Cytochem.* 30(12):1297–1300.

Benet et al., 1990, "Pharmacokinetics: The Dynamics of Drug Absorption, Distribution, and Elimination," in *Goodman and Gilman's The Pharmacological Basis of Therapeutics*, Gilman et al., eds., Pergamon Press, New York, pp. 3–32.

Ebadi, M., 1998, "The Pharmacokinetic Basis of Therapeutics," in *CRC Desk Reference of Clinical Pharmacology*, CRC Press LLC, Boca Raton, pp. 1–7.

(List continued on next page.)

*Primary Examiner*—Laurie Scheiner
*Assistant Examiner*—Jeffrey S. Parkin
(74) *Attorney, Agent, or Firm*—John P. White; Cooper & Dunham LLP

(57) ABSTRACT

Previous studies of human immunodeficiency virus type 1 (HIV-1) envelope glycoprotein-mediated membrane fusion have focused on laboratory-adapted T-lymphotropic strains of the virus. The goal of this application was to develop a novel screening assay to characterize membrane fusion mediated by a primary HIV-1 isolate in comparison with a laboratory-adapted strain. To this end, a novel fusion assay was developed on the basis of the principle of resonance energy transfer, using HeLa cells stably transfected with gp120/gp41 from the T-lymphotropic isolate HIV-$1_{LA1}$ or the macrophage-tropic primary isolate HIV-$1_{JR-FL}$. These cells fused with CD4+ target cell lines with a tropism mirroring that of infection by the two viruses. Of particular note, HeLa cells expressing HIV-$1_{JR-FL}$ gp120/gp41 fused only with PM1 cells, a clonal derivative of HUT 78, and not with other T-cell or macrophage cell lines. These results demonstrate that the envelope glycoproteins of these strains play a major role in mediating viral tropism. Despite significant differences exhibited by HIV-$1_{JR-FL}$ and HIV-$1_{LAI}$ in terms of tropism and sensitivity to neutralization by CD4-based proteins, the present study found that membrane fusion mediated by the envelope glycoproteins of these viruses had remarkably similar properties. In particular, the degree and kinetics of membrane fusion were similar, fusion occurred at neutral pH and was dependent on the presence of divalent cations. The claimed invention will facilitate the screening and identification of novel agents that are capable of inhibiting these interactions.

9 Claims, 5 Drawing Sheets

OTHER PUBLICATIONS

Allan, J., 1997, "Human Immunodeficiency Virus–Related Infections in Animal Model Systems," in *AIDS: Biology, Diagnosis, Treatment, and Prevention,* fourth edition, De Vita, Jr., et al., eds., Lippincott–Raven Publishers, Philadelphia, pp. 15–27.

Hirsch et al., 1997, "Antiretroviral Therapy," in *AIDS: Biology, Diagnosis, Treatment, and Prevention, fourth edition,* De Vita, Jr., et al., eds., Lippincott–Raven Publishers, Philadelphia, pp. 495–508.

Stein et al., 1993, "Immune–Based Therapeutics: Scientific Rationale and Promising Approaches to the Treatment of the Human Immunodeficiency Virus–Infected Individual," Clin. Infect. Dis. 17:749–771.

Sinangil et al., 1988, "Quantitative Measurement of Fusion Between Human Immunodeficiency Virus and Cultured Cells Using Membrane Fluorescence Dequenching," Fed. Eur. Biochem. Soc. 239:88–92.

Dimitrov et al., 1991, "Initial Stages of HIV–1 Envelope Glycoprotein–Mediated Cell Fusion Monitored bya New Assay Based on Redistribution of Fluorescent Dyes," AIDS Res. Human Retro. 7:799–805.

Chams et al., 1992, "Simple Assay to Screen for Inhibitors of Interaction Between the Human Immunodeficiency Virus Envelope Glycoprotein and It's Cellular Receptor, CD4," Antimicrob. Agents Chem. 36:267–272.

Szabo et al., 1992, "CD4 Changes Conformation Upon Ligand Binding," J. Immunol. 149:3596–3604.

O'Brien et al., 1990, "HIV–1 Tropism for Mononuclear Phagocytes can be Determined by Regions of gp120 Outside of the CD4–binding Domain," Nature 348:69–73.

Crowe, S.M., et al., 1992, "Human immunodeficiency virus-infected monocyte–derived macrophages express surface gp120 and fuse with CD4 lymphoid cells in vitro: a possible mechanism of T lymphocyte depletion in vivo.", ; Immunology and Immunopathology. vol. 65, No. 2, pp. 143–151.

Schmidtmayerova, H., et al., 1993, "Characterization of HIV1–PAR a macrophage–tropic strain: cell tropism, virus/cell entry and nucleotide sequence of the envelope glycoprotein.", Research in Virology. vol. 144, No. 1, pp. 21–26.

RET
Time Course

RET
Inhibition

FLUORESCENCE RESONANCE ENERGY TRANSFER SCREENING ASSAY FOR THE IDENTIFICATION OF COMPOUNDS THAT ARE CAPABLE OF ABROGATING MACROPHAGE-TROPIC HIV-1 CELL FUSION

This application is a National Stage entry of International Application No. PCT/US96/09894, filed Jun. 7, 1996, which is a Continuation-In-Part of application U.S. Ser. No. 08/475,515, filed Jun. 7, 1995, the content of which is hereby incorporated into this application by reference.

BACKGROUND OF THE INVENTION

Throughout this application, various publications are referenced. The disclosure of these publications is hereby incorporated by reference into this application to describe more fully the art to which this invention pertains.

HIV infects primarily helper T lymphocytes and monocytes/macrophages—cells that express surface CD4—leading to a gradual loss of immune function which results in the development of the human acquired immune deficiency syndrome (AIDS). The initial phase of the HIV replicative cycle involves the high affinity interaction between the HIV exterior envelope glycoprotein gp120 and the cellular receptor CD4 (Klatzmann, D. R., et al., Immunodef. Rev. 2, 43–66 (1990)). Following the attachment of HIV to the cell surface, viral and target cell membranes fuse, resulting in the introduction of the viral genome into the cytoplasm. Several lines of evidence demonstrate the requirement of this interaction for viral infectivity. In vitro, the introduction of a functional cDNA encoding CD4 into human cells which do not normally express CD4 is sufficient to render these otherwise resistant cells susceptible to HIV infection (Maddon, P. J., at al., Cell 47,1 333–348 (1986)).

Characterization of the interaction between HIV gp120 and CD4 has been facilitated by the isolation of cDNA clones encoding both molecules (Maddon, P. J., et al., Cell 42, 93–104 (1985), Wain-Hobson, S., et al., Cell 40, 9–17 (1985)). CD4 is a nonpolymorphic, lineage-restricted cell surface glycoprotein that is a member of the immunoglobulin gene superfamily. High-level expression of both full-length and truncated, soluble versions of CD4 (sCD4) have been described in stable expression systems. The availability of large quantities of purified sCD4 has permitted a detailed understanding of the structure of this complex glycoprotein. Mature CD4 has a relative molecular weight of 55,000 and consists of an amino-terminal 372 amino acid extracellular domain containing four tandem immunoglobulin-like regions denoted V1–V4, followed by a 23 amino acid transmembrane domain and a 38 amino acid cytoplasmic segment. Experiments using truncated sCD4 proteins demonstrate that the determinants of high-affinity binding to HIV gp120 lie within the amino-terminal immunoglobulin-like domain V1 (Arthos, J., et al., Cell 57, 469–481 (1989)). Mutational analysis of V1 has defined a discrete gp120-binding site (residues 38–52 of the mature CD4 protein) that comprises a region structurally homologous to the second complementarity-determining region (CDR2) of immuno-globulins (Arthos, J., et al., Cell 57, 469–481 (1989)).

The HIV-1 envelope gene env encodes an envelope glycoprotein precursor, gp160, which is cleaved by cellular proteases before transport to the plasma membrane to yield gp120 and gp41. The membrane-spanning glycoprotein, gp41, is non-covalently associated with gp120, a purely extracellular glycoprotein. The mature gp120 molecule is heavily glycosylated (approximately 24 N-linked oligosaccharides), contains approximately 480 amino acid residues with 9 intra-chain disulfide bonds (Leonard, C. K., et. al., J. Biol. Chem. 265, 10373–10382 (1990)), and projects from the viral membrane as a dimeric or multimeric molecule (Earl, P. L., et. al. Proc. Natl. Acad. Sci. U.S.A. 87, 648–652 (1990)).

Mutational studies of HIV-1 gp120 have delineated important functional regions of the molecule. The regions of gp120 that interact with gp41 map primarily to the N- and C-termini (Helseth, E., et. al., J. Virol. 65, 2119–2123 (1991)). The predominant strain-specific neutralizing epitope on gp120 is located in the 32–34 amino acid residue third variable loop, herein referred to as the V3 loop, which resides near the center of the gp120 sequence (Bolognesi, D.P. TIBTech 8, 40–45 (1990)). The CD4-binding site maps to discontinuous regions of gp120 that include highly conserved or invariant amino acid residues in the second, third, and fourth conserved domains (the C2, C3 and C4 domains) of gp120 (Olshevsky, U., et al. J. Virol. 64, 5701–5707 (1990)). It has been postulated that a small pocket formed by these conserved residues within gp120 could accommodate the CDR2 loop of CD4, a region defined by mutational analyses as important in interacting with gp120 (Arthos, J., et al., Cell 57, 469–481 (1989)).

Following the binding of HIV-1 gp120 to cell surface CD4, viral and target cell membranes fuse, resulting in the introduction of the viral capsid into the target cell cytoplasm (Maddon, P. J. et al., Cell 54:865 (1988)). Most evidence to date indicates that HIV-1 fusion is pH-independent and occurs at the cell surface. The HIV-1 fusion protein is gp41, the transmembrane component of the envelope glycoprotein. This protein has a hydrophobic fusion peptide at the amino-terminus and mutations in this peptide inhibit fusion (Kowalski, M. et al., Science 237:1351 (1987)). In addition to gp41, recent observations suggest that gp120 plays a role in membrane fusion distinct from its function in attachment. For example, antibodies to the principle neutralizing epitope on gp120, the V3 loop, can block infection without inhibiting attachment (Skinner, M. A. et al., J. Virol. 62:4195 (1988)). In addition, mutations in the tip of this loop reduce or prevent syncytia formation in HeLa-CD4 cells expressing the mutated gp120/gp41 molecules (Freed, E. O. et al., J. Virol. 65:190 (1991)).

Several lines of evidence have implicated molecules in addition to CD4 and gp120/gp41 in HIV-1 induced membrane fusion. For example, recent studies have indicated that human cells may contain an accessory molecule, not present in non-primate cells, which is required for HIV-1 fusion (Dragic, T. et al., J. Virol. 66:4794 (1992)). The nature of this accessory molecule or molecules is unknown. While some studies have postulated it might be a cell surface protease (Hattori, T. et al., Febs. Lett. 248:48 (1989)), this has yet to be confirmed.

Fusion of the HIV-1 virion with the host cell plasma membrane is mimicked in many ways by the fusion of HIV-1 infected cells expressing gp120/gp41 with uninfected cells expressing CD4. Such cell-to-cell fusion results in the formation of multinucleated giant cells or syncytia, a phenomenon observed with many viruses which fuse at the cell surface. Much of our current understanding of HIV-1-induced membrane fusion is derived from studies of syncytium formation. For example, this approach was used to demonstrate that expression of HIV-1 gp120/gp41 in a membrane, in the absence of any other viral protein, is necessary and sufficient to induce fusion with a CD4$^+$ membrane (Lifson, J. D. et al., Nature 323:725 (1986)).

Compared with virion fusion to cells, syncytium formation induced by HIV-1 appears to involve an additional step. First, the gp120/gp41-bearing membrane fuses with the CD4– bearing membrane. This is a rapid and reversible process which connects the membranes at localized sites and allows membrane-bound dyes to flow from one cell to the other (Dimitrov, D. et al., AIDS Res. Human Retroviruses 7:799 (1991)). This step presumably parallels the attachment of a virion to a $CD4^+$ cell and the fusion therebetween. The second stage in cells fusion is the irreversible fusion of cells to form syncytia. The efficiency of this process is increased by the interaction of cellular adhesion molecules such as ICAM-1 and LFA-1, although these molecules are not absolutely required for syncytium formation to proceed (Golding, H. et al., AIDS Res. Human Retroviruses 8:1593 (1992)).

Most of the studies of HIV-1 fusion, including those discussed above, have been performed with strains of HIV-1 which have been extensively propagated in transformed human T cell lines. These strains, known as laboratory-adapted strains, differ in several important characteristics from primary or clinical isolates of the virus obtained from HIV-1 infected individuals (O'Brien, W. A. et al., Nature 348:69 (1990)). Some examples of these differences are listed in the table below.

| Laboratory adapted Strains | Primary Isolates |
|---|---|
| tropic for transformed T cell lines, do not infect primary monocytes | many are tropic for primary monocytes and do not infect transformed T cell lines |
| very sensitive to neutralization by soluble CD4 | relatively insensitive to neutralization by sCD4 |
| gp120 spontaneously dissociates from gp41, and this stripping is increased by sCD4 | little spontaneous stripping and sCD4 only causes stripping at 4° C., not at 37° C. |

These differences are mirrored by differences in the primary sequence of the viral proteins, and in particular of the envelope glycoproteins. In some cases, the different tropisms of primary isolates and laboratory-adapted strains of HIV-1 have been mapped to regions on gp120 such as the V3 loop (O'Brien, W. A. et al., Nature 348:69 (1990)). It is possible that different V3 loops interact with different accessory molecules on T cell lines or monocytes, thereby mediating tropism.

HIV-1 envelope-mediated cell fusion is a model for the early stages of HIV-1 infection and can be used as an assay for anti-viral molecules which block HIV-1 attachment and fusion (Sodroski, J. et al., Nature 322–470 (1986), Lifson, J. D. et al., Nature 323:725 (1986)). Moreover, HIV-1 induced cell fusion is important in its own right as a potential mechanism for the pathogenesis of HIV-1 infections. It is a mode of transmission of HIV-1 from infected to uninfected cells (Gupta, P. et al., J. Virol. 63:2361 (1989), Sato, H. et al., Virology 186:712 (1992)) and by this mechanism, it could contribute to the spread of HIV-1 throughout the body of the infected individual. Cell fusion is also a direct mechanism of HIV-1-induced cell death (Sodroski, J. et al., Nature 322:470 (1986), Lifson, J. D. et al., Nature 323:725 (1986)). Syncytia are seen in vivo, notably in the brains of AIDS patients suffering from neurological complications such as AIDS dementia complex (Pumarola-Sune, T. et al., Ann. Neurol. 21:490 (1987)). In addition, syncytia have been observed in the spleens of HIV-1-infected individuals (Byrnes, R. K. et al., JAMA 250:1313 (1983)). It is possible that cell fusion may play a role in the depletion of $CD4^+$ T lymphocytes that is characteristic of the pathogenic process leading to AIDS (Haseltine, W. A. in AIDS and the new viruses, Dalgleish, A. G. and Weiss, R. A. eds. (1990)).

In this context, it may be significant that HIV-1 isolates from asymptomatic HIV-1-infected individuals often infect cells in vitro without inducing syncytia. In contrast, clinical isolates from patients with ARC and AIDS are commonly highly virulent, syncytia-inducing strains (Tersmette, M. et al., J. Virol. 62:2026 (1988)). In addition, there is often a switch from non-syncytium inducing (NSI) to syncytium-inducing (SI) isolates within patients as the disease progresses and symptoms appear (Tersmette, M. et al., J. Virol. 63:2118 (1989), Cheng-Mayer, C. et al., science 240:80 (1988)). It is not clear why some HIV-1 strains do not induce syncytia, although it is possible that cells infected with these strains do not express sufficient levels of gp120/gp41 for cell fusion to occur, by analogy with some other fusogenic viruses. However, it is believed that this switch from NSI to SI HIV-1 strains influences the clinical course of HIV-1 infection. The presence of naturally occurring anti-syncytia antibodies in some subjects may delay the development of HIV-1 related diseases in these subjects (Brenner, T. J. et al., Lancet 337:1001 (1991)).

The development of methods for measuring HIV-1 envelope glycoprotein-mediated membrane fusion serves a useful role in further elucidating the mechanism of HIV-1 infection, and enabling the identification of agents which alter HIV-1 envelope glycoprotein-mediated cell fusion. At present there exist several potential methods for measuring such fusion.

The first is an assay of HIV-1 envelope glycoprotein-mediated cell fusion in which fusion is measured microscopically by measuring the transfer of fluorescent dyes between cells (Dimitrov, D. S., et al., AIDS Res. Human Retroviruses 7: 799–805 (1991)). This technique measures dye distribution rather than fluorescence intensity and as such cannot be performed using fluorometer. The assay would not be easily automated and has not been performed with cells which stably express the HIV-1 envelope glycoprotein.

The second is an assay for HIV-1 envelope-mediated cell fusion measured between (a) cells which stably express the HIV-1 tat gene product in addition to gp120/gp41, and (b) $CD4^+$ cells which contain a construct consisting of the β-galactosidase gene under the control of the HIV-1 LTR promotor. When these cells fuse, β-galactosidase is expressed and can be measured using an appropriate soluble or insoluble chromogenic substrate (Dragic, T., et al., Journal of Virology 66:4794 (1992)). This assay takes at least 1 day to perform and cannot easily be adapted to new target cells such as primary macrophage cells. This assay also does not measure cell fusion in real time and is thus not amenable to use in analyzing fusion kinetics.

Finally, the third is a fluorescence dequenching assay for the fusion of HIV-1 virions to cells (Sinangil, F., et al., FEBS Letters 239:88–92 (1988)). This assay requires the use of purified HIV-1 virions, and both the purification of HIV-1 virions and the assay must be performed in a containment facility. It would be difficult to readily isolate sufficient quantities of clinical virus isolates to perform the assay. Furthermore, this assay is more complicated and less reproducible than a RET assay using cells which stably express HIV-1 envelope glycoproteins and CD4.

The methods of the subject invention employ a resonance energy transfer (RET) based assay which overcomes the problems inherent in the above-identified methods for measuring HIV-1 envelope glycoprotein-mediated membrane fusion. Specifically, the methods of the subject invention employ a RET assay which is rapid, reproducible, quantitative, adaptable to various cell types, and relatively safe, and can be automated.

SUMMARY OF THE INVENTION

The subject invention provides a method for determining whether an agent is capable of specifically inhibiting the fusion of an HIV-1 envelope glycoprotein$^+$ cell with an appropriate CD4$^+$ cell which comprises: (a) contacting a sample containing a suitable amount of the agent with a suitable amount of the appropriate CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the absence of the agent, the cell membranes of the CD44 cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; (c) comparing the percent resonance energy transfer value so determined with a known standard, so as to determine whether the agent is capable of inhibiting fusion of the CD4$^+$ cell with the HIV-1 envelope glycoprotein$^+$ cell; and (d) determining whether the agent inhibits the fusion of a first control cell with a second control cell under conditions which would permit non-HIV-1 envelope glycoprotein-mediated fusion of the first and second control cells in the absence of the agent, so as to determine whether the agent is capable of specifically inhibiting the fusion of the CD4$^+$ cell with the HIV-1 envelope glycoprotein$^+$ cell.

The subject invention also provides a method for determining whether an agent is capable of specifically inhibiting the infection of a CD4$^+$ cell with HIV-1 which comprises determining whether the agent is capable of specifically inhibiting the fusion of a CD4$^+$ cell with an HIV-1 envelope glycoprotein$^+$ cell by the method of the subject invention, so as to thereby determine whether the agent is capable of specifically inhibiting the infection of a CD4$^+$ cell with HIV-1.

The subject invention further provides a method for determining whether an agent is capable of inhibiting the fusion of an HIV-1 envelope glycoprotein$^+$ cell with an appropriate CD4$^+$ cell which comprises: (a) contacting a sample containing a suitable amount of the agent with a suitable amount of the CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the absence of the agent, the cell membranes of the CD4$^+$ cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; and (c) comparing the percent resonance energy transfer value so determined with a known standard, so as to determine whether the agent is capable of inhibiting fusion of the CD4$^+$ cell with the HIV-1 envelope glycoprotein$^+$ cell.

This invention also provides an agent determined by the above-described method.

The subject invention further provides a method for quantitatively determining the ability of an antibody-containing sample to specifically inhibit the fusion of an HIV-1 envelope glycoprotein$^+$ cell with an appropriate CD4$^+$ cell which comprises: (a) contacting a predetermined amount of the antibody-containing sample with a suitable amount of the CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the absence of the antibody-containing sample, the cell membranes of the CD4$^+$ cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; (c) comparing the percent resonance energy transfer value so determined with a known standard, so as to quantitatively determine the ability of the antibody-containing sample to inhibit the fusion of the CD4$^+$ cell with the HIV-1 envelope glycoprotein$^+$ cell; and (d) determining whether the antibody-containing sample inhibits the fusion of a first control cell with a second control cell under conditions which would permit non-HIV-1 envelope glycoprotein-mediated fusion of the first and second control cells in the absence of the agent, so as to quantitatively determine the ability of the antibody-containing sample to specifically inhibit the fusion of the CD4$^+$ cell with the HIV-1 envelope glycoprotein$^+$ cell.

The subject invention further provides a method for quantitatively determining the ability of an antibody-containing sample to inhibit the fusion of an HIV-1 envelope glycoprotein$^+$ cell with an appropriate CD4$^+$ cell which comprises: (a) contacting a predetermined amount of the antibody-containing sample with a suitable amount of the CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the -absence of the antibody-containing sample, the cell membranes of the CD4$^+$ cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after, a suitable period of time; and (c) comparing the percent resonance energy transfer value so determined with a known standard, so as to quantitatively determine the ability of the antibody-containing sample to inhibit the fusion of the CD4$^+$ cell with the HIV-1 envelope glycoprotein$^+$ cell.

The subject invention further provides a method for determining the stage or clinical prognosis of an HIV-1 infection in an HIV-1-infected subject which comprises: (a) obtaining an antibody-containing sample from the HIV-1-infected subject; (b) quantitatively determining the ability of the antibody-containing sample so obtained to inhibit the fusion of a CD4$^+$ cell with an HIV-1 envelope glycoprotein$^+$ cell by the method of the subject invention; and (c) comparing the ability of the antibody-containing sample to inhibit the fusion of the CD4$^+$ cell with the HIV-1 envelope glycoprotein$^+$ cell so determined with that of an antibody-containing sample obtained from an HIV-1-infected subject having an HIV-1 infection at a known stage or having a known clinical prognosis, so as to determine the stage or clinical prognosis of the HIV-1 infection in the HIV-1-infected subject.

The subject invention further provides a method for determining the efficacy of an anti-HIV-1 vaccination in a vaccinated, non-HIV-1-infected subject which comprises: (a) obtaining an antibody-containing sample from the vaccinated, non-HIV-1-infected subject; (b) quantitatively determining the ability of the antibody-containing sample so obtained to inhibit the fusion of an HIV-1 envelope glycoprotein$^+$ cell with an appropriate CD4$^+$ cell by the method of the subject invention; and (c) comparing the ability of the antibody-containing sample to inhibit the fusion of the CD4$^+$ cell with the HIV-1 envelope glycoprotein$^+$ cell so determined with that of an antibody-containing sample obtained from a vaccinated, non-HIV-1-infected subject for whom the anti-HIV-1 vaccination has a known efficacy, so as to determine the efficacy of the anti-HIV-1 vaccination in the vaccinated, non-HIV-1-infected subject.

The subject invention further provides a kit for determining whether an agent is capable of specifically inhibiting the fusion of an HIV-1 envelope glycoprotein$^+$ cell with an appropriate CD4$^+$ cell which comprises, in separate compartments: (a) a suitable amount of a CD$^+$ cell whose cell membrane is labeled with a first dye; (b) a suitable amount of an HIV-1 envelope glycoprotein$^+$ cell whose cell membrane is labeled with a second dye, the HIV-1 envelope glycoprotein$^+$ cell being capable of fusing with the CD4$^+$ cell of (a) under suitable conditions in the absence of the agent, and the first and second dyes permitting resonance energy transfer therebetween only when juxtaposed within the same membrane; (c) a suitable amount of a first control cell whose cell membrane is labeled with the first dye; and (d) a suitable amount of a second control cell whose cell membrane is labeled with the second dye, the second control cell being capable of non-HIV-1 envelope glycoprotein-mediated fusion with the first control cell of (c) under suitable conditions in the absence of the agent.

The subject invention further provides a kit for determining whether an agent is capable of inhibiting the fusion of a CD4$^+$ cell with an HIV-1 envelope glycoprotein$^+$ cell which comprises, in separate compartments: (a) a suitable amount of a CD4$^+$ cell whose cell membrane is labeled with a first dye; and (b) a suitable amount of an HIV-1 envelope glycoprotein$^+$ cell whose cell membrane is labeled with a second dye, the HIV-1 envelope glycoprotein$^+$ cell being capable of fusing with the CD4$^+$ cell of (a) under suitable conditions in the absence of the agent, and the first and second dyes permitting resonance energy transfer therebetween only when juxtaposed within the same membrane.

The subject invention further provides a method for determining whether an HIV-1 isolate is syncytium-inducing which comprises: (a) obtaining a sample of an HIV-1 isolate envelope glycoprotein$^+$ cell whose cell membrane is labeled with a first dye; (b) contacting a suitable amount of the sample with a suitable amount of a CD4$^+$ cell under conditions which would permit the fusion of the CD4$^+$ cell with a syncytium-inducing HIV-1 strain envelope glycoprotein$^+$ cell, the cell membrane of the CD4$^+$ cell being labeled with a second dye which permits resonance energy transfer between the first dye only when the first and second dyes are juxtaposed within the same membrane; (c) determining the percent resonance energy transfer value of the resulting sample after a suitable period of time; and (d) comparing the percent resonance energy transfer value so determined with a known standard, so as to determine whether the HIV-1 isolate is syncytium-inducing.

Finally, the subject invention provides a method for determining the stage of an HIV-1 infection in an HIV-1-infected subject which comprises determining by the method of the subject invention whether the HIV-1 isolate with which the HIV-1 infected subject is infected is syncytium inducing, so as to thereby determine the stage of the HIV-1 infection in the HIV-1-infected subject.

Figure 1:
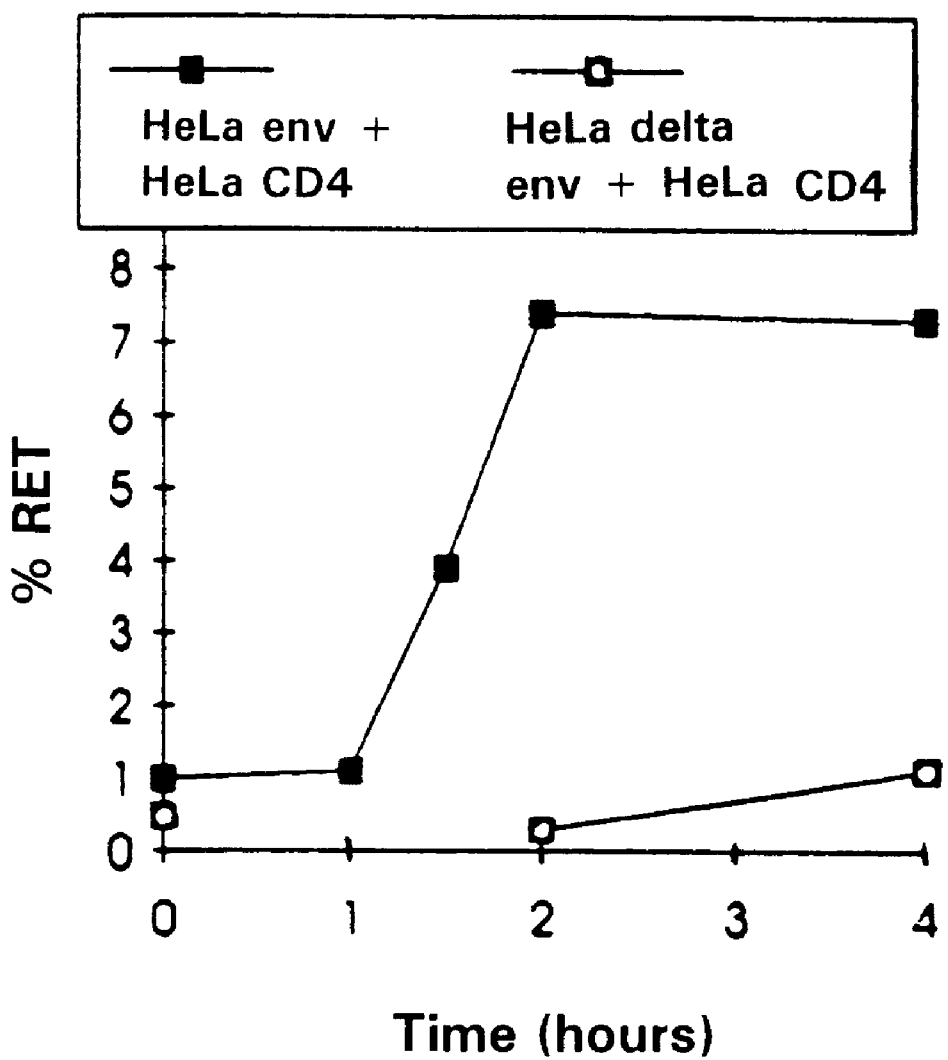
FIG. 1 Time course of fusion between HeLa-env$^+$ cells and HeLa-CD4$^+$ cells measured by the RET assay.

$$\% \text{ inhibition of RET} = [(A-B)/(A-C)] * 100.$$

Where A is the maximum % RET in the absence of antibody, B is the % RET following incubation with OKT4A and C is the background % RET determined using HeLa cells in place of HeLa-env$_{LAI}{}^+$ or HeLa-env$_{JR-FL}{}^+$ cells.

DETAILED DESCRIPTION OF THE INVENTION

The plasmid designated pMA243 was deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. 75626. The plasmid pMA243 was deposited with the ATCC on December 16, 1993.

This invention provides a method for determining whether an agent is capable of inhibiting the fusion of a macrophage-tropic primary isolate of HIV-1 to a CD4$^+$ cell which comprises: (a) contacting (i) an appropriate CD4$^+$ cell, which is labeled with a first dye, with (ii) a cell expressing the HIV-1 envelope glycoprotein of the macrophage-tropic primary isolate of HIV-1 on its surface, which is labeled with a second dye, in the presence of an excess of the agent under conditions permitting the fusion of the CD4$^+$ cell to the cell expressing the HIV-1 envelope glycoprotein on its surface in the absence of the agent, the first and second dyes being selected so as to allow resonance energy transfer between the dyes; (b) exposing the product of step (a) to conditions which would result in resonance energy transfer if fusion has occurred; and (c) determining whether there is a reduction of resonance energy transfer, when compared with the resonance energy transfer in the absence of the agent, a decrease in transfer indicating that the agent is capable of inhibiting fusion of HIV-1 to CD4$^+$ cells.

The subject invention provides a method for determining whether an agent is capable of specifically inhibiting the fusion of an HIV-1 envelope glycoprotein$^+$ cell with an appropriate CD4$^+$ cell which comprises: (a) contacting a sample containing a suitable amount of the agent with a suitable amount of the appropriate CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the absence of the agent, the cell membranes of the CD4$^+$ cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; (c) comparing the percent resonance energy transfer value so determined with a known standard, so as to determine whether the agent is capable of inhibiting fusion of the CD4$^+$ cell with the HIV-1 envelope glycoprotein$^+$ cell; and (d) determining whether the agent inhibits the fusion of a first control cell with a second control cell under conditions which would permit non-HIV-1 envelope glycoprotein-mediated fusion of the first and second control cells in the absence of the agent, so as to determine whether the agent is capable of specifically inhibiting the fusion of the CD4$^+$ cell with the HIV-1 envelope glycoprotein$^+$ cell.

This invention provides an agent determined to be capable of specifically inhibiting the fusion of an HIV-1 envelope glycoprotein$^+$ cell with an appropriate CD4$^+$ cell using the above-described method.

This invention provides a therapeutic agent determined to be capable of specifically inhibiting the fusion of an HIV-1 envelope glycoprotein$^+$ cell with an appropriate cell using the above-described method.

As used herein, the term "agent" includes both protein and non-protein moieties. In one embodiment, the agent is a small molecule. In another embodiment, the agent is a protein. The protein may be, by way of example, an antibody directed against a portion of an HIV-1 envelope glycoprotein, e.g., gp120. The agent may be derived from a library of low molecular weight compounds or a library of extracts from plants or other organisms. In an embodiment, the agent is known. In a separate embodiment, the agent is not previously known.

As used herein, "capable of specifically inhibiting the fusion of an HIV-1 envelope glycoprotein$^+$ cell with an appropriate CD4$^+$ cell" means (a) capable of reducing the rate of fusion of a CD4$^+$ cell membrane with HIV-1 envelope glycoprotein$^+$ cell membrane by at least 5%, but not capable of reducing the rate of non-CD4/HIV-1 envelope glycoprotein-mediated cell membrane fusion, or (b) capable of reducing by at least 5% the total amount of fusion of a CD4$^+$ cell membrane with HIV-1 envelope glycoprotein$^+$ cell membrane occurring by the endpoint of fusion, but not capable of reducing the total amount of non-CD4/HIV-1 envelope glycoprotein-mediated cell membrane fusion occurring by the endpoint of fusion. As used herein, the rate of cell membrane fusion means the total quantity of cell membrane fused per unit of time. As used herein, the "endpoint of fusion" means the point in time at which all fusion of CD4$^+$ cell membrane with HIV-1 envelope glycoprotein$^+$ cell membrane capable of occurring has occurred.

An example of the method of the subject invention is provided infra. A known amount of HIV-1 envelope glycoprotein$^+$ cell is contacted with a known amount of CD4$^+$ cell together with an agent under conditions which would permit the fusion of Y amount of cell membrane per unit of time in the absence of the agent, wherein Y is equal to the sum of the amounts of CD4$^+$ cell membrane and HIV-1 envelope glycoprotein$^+$ cell membrane, e.g., 0.5×Y CD4$^+$ cell membrane+0.5×Y HIV-1 envelope glycoprotein$^+$ cell membrane. In the presence of the agent, 0.2×Y amount of cell membrane fuses per unit of time. The agent is shown not to reduce the rate of non-CD4/HIV-1 envelope glycoprotein-mediated cell membrane fusion. Accordingly, the agent specifically inhibits the fusion of a CD4$^+$ cell with an HIV-1 envelope glycoprotein$^+$ cell.

As used herein, the fusion of CD4$^+$ cell membrane with HIV-1 envelope glycoprotein$^+$ cell membrane means the hydrophobic joining and integration of CD4$^+$ cell membrane with HIV-1 envelope glycoprotein$^+$ cell membrane to form a hybrid membrane comprising components of both cell membranes, and does not mean the CD4/HIV-1 envelope glycoprotein-mediated adhesion therebetween, which adhesion is a prerequisite for the fusion.

As used herein, the term "CD4" includes (a) native CD4 protein and (b) a membrane-bound CD4-based protein. As used herein, a membrane-bound CD4-based protein is any membrane-bound protein, other than native CD4, which comprises at least that portion of native CD4 which is required for native CD4 to form a complex with the HIV-1 gp120 envelope glycoprotein. In one embodiment, the CD4-based protein comprises a portion of a non-CD4 protein. If the CD4-based protein comprises a portion of a non-CD4 protein, then the portion of native CD4 which is required for native CD4 to form a complex with the HIV-1 gp120 envelope glycoprotein is the portion of native CD4 having the amino acid sequence from +1 to about +179.

As used herein, the word "cell" includes a biological cell, e.g., a HeLa cell, and a non-biological cell, e.g., a lipid vesicle (e.g., a phospholipid vesicle) or virion.

As used herein, a CD4$^+$ cell is a cell having CD4 affixed to the surface of its cell membrane, wherein the appropriate CD4$^+$ cell is capable of specifically binding to and fusing with an HIV-1 envelope glycoprotein$^+$ cell exposed thereto. In one embodiment, the suitable CD4$^+$ cell is a CD4$^+$ HeLa cell. In another embodiment, the suitable CD4$^+$ cell is a PM1 cell. In a further embodiment, the CD4$^+$ cell is a primary human T lymphocyte. In a still further embodiment, the CD4$^+$ cell is a primary human macrophage.

As used herein, an HIV-1 envelope glycoprotein$^+$ cell is a cell having HIV-1 envelope glycoprotein affixed to the surface of its cell membrane so as to permit the HIV-1 envelope glycoprotein$^+$ cell to specifically bind to and fuse with an appropriate CD4$^+$ cell exposed thereto. In one embodiment, the HIV-1 envelope glycoprotein$^+$ cell is an HIV-1 envelope glycoprotein$^+$ HeLa cell. In another embodiment, the HIV-1 envelope glycoprotein$^+$ cell is HIV-1.

Each HIV-1 isolate is tropic for a limited number of CD4$^+$ cell types. Accordingly, in the subject invention, the fusion of a CD4$^+$ cell with an HIV-1 envelope glycoprotein$^+$ cell means the fusion of a CD4$^+$ cell with an HIV-1 envelope glycoprotein$^+$ cell, which HIV-1 envelope glycoprotein corresponds to an envelope glycoprotein from an HIV-1 isolate tropic for the CD4$^+$ cell. For example, the HIV-1 isolates$_{JR\text{-}FL}$, JR-CSF and BaL are tropic for CD4$^+$ primary human macrophages, the HIV-1 isolates LAI and IIIB are tropic for human CD4$^+$ T lymphocyte cell lines and HeLa-CD4 cells, and the RIV-1 isolates MN and SF-2 are tropic for human CD4+ T lymphocyte cell lines. The HIV-1 isolates$_{JR-FL}$, JR-CSF, BaL, LAI, IIIB, MN and SF-2 may also be tropic for CD4+ cell types other than those enumerated supra.

As used herein, an appropriate CD4+ cell line is a cell line that fuses with the HIV-1 envelope glycoprotein+ cell line, such that the % RET measurement obtained is at least 5 fold greater than the background level obtained using a combination of cells which do not fuse (e.g. HeLa cells mixed with the CD4+ cell line). Moreover, the % RET obtained using the CD4+ cell line and the HIV-1 envelope glycoprotein+ cell line should be inhibited to background levels using 1ug/ml OKT4A.

The suitable amounts of agent, CD4+ cell and HIV-1 envelope glycoprotein+ cell may be determined according to methods well known to those skilled in the art.

Conditions which would permit the fusion of the appropriate CD4+ cell with the HIV-1 envelope glycoprotein+ cell in the absence of the agent are well known to those skilled in the art.

As used herein, a cell "labeled" with a dye means a cell having a dye integrated into its cell membrane, i.e., a cell having dye molecules commingled with the lipid molecules of its cell membrane.

Resonance energy transfer is defined as follows: For juxtaposed dyes D1, having excitation and emission spectra Ex1 and Em1, respectively, and D2, having excitation and emission spectra Ex2 and Em2, respectively, wherein (a) Em1 has a higher average frequency than that of Em2 and (b) Em1 and Ex2 overlap, resonance energy transfer is the transfer of electromagnetic energy from D1 to D2 at a frequency within the Em1 and Ex2 overlap, which resonance energy transfer (a) results from the electromagnetic excitation of D1 at a frequency within the Ex1 spectrum and (b) causes the subsequent emission of electromagnetic energy from D2 at a frequency within the Em2 spectrum. Accordingly, resonance energy transfer between D1 and D2 can be detected by exciting D1 with electromagnetic energy at a frequency within Exx1 and measuring the subsequently emitted electromagnetic energy at a frequency within Em2, the emission of electromagnetic energy at a frequency within Em2 indicating the occurrence of resonance energy transfer between D1 and D2.

The first and second dyes are "juxtaposed within the same membrane" if they are present within the same lipid membrane at a suitably short distance from each other, which suitably short distance may be readily determined by one skilled in the art.

In the subject invention, determining the percent resonance energy transfer value may be performed according to methods well known to those skilled in the art. In one embodiment, the percent resonance energy transfer value is determined by: (1) determining the resonance energy transfer value (RET) by subtracting from the total emission from D1 and D2 at a frequency within Em2 the electromagnetic energy emission due to direct D1 and D2 emission following excitation at a frequency within Ex1 and emission at the frequency within Em2, which D1 and D2 emissions are measured by separately measuring the electromagnetic energy emission due to cells labeled with each dye; and (2) determining the percent resonance energy transfer value (% RET value) by dividing the resonance energy transfer value obtained in step (1) by the total D2 emission at the frequency within Em2.

The suitable period of time after which the percent resonance energy transfer value of the resulting sample is determined may be determined according to methods well known to those skilled in the art.

The known standard is a percent resonance energy transfer value obtained using the CD4+ cell, the HIV-1 envelope glycoprotein+ cell, and an agent having a known ability to inhibit the fusion thereof.

In the subject invention, the first control cell and second control cell are capable of fusing with each other via non-HIV-1 envelope glycoprotein-mediated fusion both in the presence and absence of an agent capable of inhibiting HIV-1 envelope glycoprotein-mediated fusion, and are not capable of fusing via HIV-1 envelope glycoprotein-mediated fusion. Such cells are will known to those skilled in the art, and include, by way of example, HeLa cells which can be induced to fuse with each other by incubation at 37° C. with polyethylene glycol 1000 or with Sendai virus. These methods of inducing fusion of HeLa cells are well known to those skilled in the art.

In one embodiment, the agent is an antibody. As used in the subject invention, the term "antibody" includes, but is not limited to, both naturally occurring and non-naturally occurring antibodies. Specifically, the term "antibody" includes polyclonal and monoclonal antibodies, and antigen-binding fragments thereof. Furthermore, the term "antibody" includes chimeric antibodies, wholly synthetic antibodies, and antigen-binding fragments thereof.

In one embodiment, the first dye is a rhodamine moiety-containing molecule and the second dye is a fluorescein moiety-containing molecule. Rhodamine moiety-containing molecules and fluorescein moiety-containing molecules are well known to those skilled in the art.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

In one embodiment, the CD4+ cell is a CD4+ HeLa cell. In another embodiment of the subject invention, the HIV-1 envelope glycoprotein+ cell is an HIV-1$_{LAI}$ gp120/gp41+ HeLa cell. In a separate embodiment, the CD4+ cell is a PM1 cell and the HIV-1 envelope glycoprotein+ cell is an HIV-1$_{JR-FL}$ gp120/gp41 HeLa cell. In a further embodiment, the CD4+ cell is a primary human T lymphocyte. In a still further embodiment, the CD4+ cell is a primary human macrophage.

The subject invention also provides a method for determining whether an agent is capable of specifically inhibiting the infection of a CD4+ cell with HIV-1 which comprises determining whether the agent is capable of specifically inhibiting the fusion of a CD4+ cell with an HIV-1 envelope glycoprotein+ cell by the method of the subject invention, so as to thereby determine whether the agent is capable of specifically inhibiting the infection of a CD4+ cell with HIV-1.

The subject invention further provides a method for determining whether an agent is capable of inhibiting the fusion of an HIV-1 envelope glycoprotein+ cell with an appropriate CD4+ cell which comprises: (a) contacting a sample containing a suitable amount of the agent with a suitable amount of the CD4+ cell and a suitable amount of the HIV-1 envelope glycoprotein+ cell under conditions which would permit the fusion of the appropriate CD4+ cell with the HIV-1 envelope glycoprotein+ cell in the absence of the agent, the cell membranes of the CD4+ cell and the HIV-1 envelope glycoprotein+ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; and (c) comparing the percent resonance energy transfer value so determined with a known standard, so as to determine whether the agent is capable of inhibiting fusion of the HIV-1 envelope glycoprotein$^+$ cell with the CD4.

As used herein, "capable of inhibiting the fusion of an HIV-1 envelope glycoprotein$^+$ cell with an appropriate CD4$^+$ cell" means capable of (a) reducing the rate of fusion of CD4$^+$ cell membrane with HIV-1 envelope glycoprotein$^+$ cell membrane by at least 5%, or (b) reducing by at least 5% the total amount of fusion of CD4$^+$ cell membrane with HIV-1 envelope glycoprotein$^+$ cell membrane occurring by the endpoint of fusion. An agent capable of inhibiting the fusion of an HIV-1 envelope glycoprotein$^+$ cell with an appropriate CD4$^+$ cell may also be capable of reducing the rate to non-CD4/HIV-1 envelope glycoprotein-mediated cell membrane fusion.

This invention provides an agent determined to be capable of inhibiting the fusion of an HIV-1 envelope glycoprotein$^+$ cell with an appropriate CD4$^+$ cell using the above-described method.

In one embodiment, the first dye is a rhodamine moiety-containing molecule and the second dye is a fluorescein moiety-containing molecule.

In one embodiment, the CD4$^+$ cell is a CD4$^+$ HeLa cell. In another embodiment of the subject invention, the HIV-1 envelope glycoprotein$^+$ cell is an HIV-$1_{LAI}$ gp120/gp41$^+$ HeLa cell. In a separate embodiment, the CD4$^+$ cell is a PM1 cell and the HIV-1 envelope glycoprotein$^+$ cell is an HIV-$1_{JR-FL}$ gp120/gp41 HeLa cell. In a further embodiment, the CD4$^+$ cell is a primary human T lymphocyte. In a still further embodiment, the CD4$^+$ cell is a primary human macrophage.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

The subject invention further provides a method for quantitatively determining the ability of an antibody-containing sample to specifically inhibit the fusion of an HIV-1 envelope glycoprotein$^+$ cell with an appropriate CD4$^+$ cell which comprises: (a) contacting a predetermined amount of the antibody-containing sample with a suitable amount of the appropriate CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the absence of the antibody-containing sample, the cell membranes of the CD4$^+$ cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; (c) comparing the percent resonance energy transfer value so determined with a known standard, so as to quantitatively determine the ability of the antibody-containing sample to inhibit the fusion of the CD4$^+$ cell with the HIV-1 envelope glycoprotein$^+$ cell; and (d) determining whether the antibody-containing sample inhibits the fusion of a first control cell with a second control cell under conditions which would permit non-HIV-1 envelope glycoprotein-mediated fusion of the first and second control cells in the absence of the agent, so as to quantitatively determine the ability of the antibody-containing sample to specifically inhibit the fusion of the CD4$^+$ cell with the HIV-1 envelope glycoprotein$^+$ cell.

The antibody-containing sample may be any antibody-containing sample. In one embodiment, the antibody-containing sample is a serum sample. In another embodiment, the antibody-containing sample is an IgG preparation. Methods of obtaining an antibody-containing sample are well known to those skilled in the art.

In one embodiment, the first dye is a rhodamine moiety-containing molecule and the second dye is a fluorescein moiety-containing molecule.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

In one embodiment, the CD4$^+$ cell is a CD4$^+$ HeLa cell. In another embodiment of the subject invention, the HIV-1 envelope glycoprotein$^+$ cell is an HIV-$1_{LAI}$ gp120/gp41$^+$ HeLa cell. In a separate embodiment, the CD4$^+$ cell is a PM1 cell and the HIV-1 envelope glycoprotein$^+$ cell is an HIV-$1_{JR-FL}$ gp120/gp41 HeLa cell. In a further embodiment, the CD4$^+$ cell is a primary human T lymphocyte. In a still further embodiment, the CD4$^+$ cell is a primary human macrophage.

The subject invention further provides a method for quantitatively determining the ability of an antibody-containing sample to inhibit the fusion of an HIV-1 envelope glycoprotein$^+$ cell with an appropriate CD4$^+$ cell which comprises: (a) contacting a predetermined amount of the antibody-containing sample with a suitable amount of the appropriate CD4$^+$ cell and a suitable amount of the HIV-1 envelope glycoprotein$^+$ cell under conditions which would permit the fusion of the CD4$^+$ cell with the HIV-1 envelope glycoprotein$^+$ cell in the absence of the antibody-containing sample, the cell membranes of the CD4$^+$ cell and the HIV-1 envelope glycoprotein$^+$ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; and (c) comparing the percent resonance energy transfer value so determined with a known standard, so as to quantitatively determine the ability of the antibody-containing sample to inhibit the fusion of the HIV-1 envelope glycoprotein$^+$ with the CD4$^+$ cell.

In one embodiment, the first dye is a rhodamine moiety-containing molecule and the second dye is a fluorescein moiety-containing molecule.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

In one embodiment, the CD4$^+$ cell is a CD4$^+$ HeLa cell. In another embodiment of the subject invention, the HIV-1 envelope glycoprotein$^+$ cell is an HIV-$1_{LAI}$ gp120/gp41$^+$ HeLa cell. In a separate embodiment, the CD4$^+$ cell is a PM1 cell and the HIV-1 envelope glycoprotein⁺-cell is an HIV-1$_{JR-FL}$ gp120/gp41 HeLa cell. In a further embodiment, the CD4⁺ cell is a primary human T lymphocyte. In a still further embodiment, the CD4⁺ cell is a primary human macrophage.

The subject invention further provides a method for determining the stage of clinical prognosis of an HIV-1 infection in an HIV-1-infected subject which comprises: (a) obtaining an antibody-containing sample from the HIV-1-infected subject; (b) quantitatively determining the ability of the antibody-containing sample so obtained to inhibit the fusion of an HIV-1 envelope glycoprotein⁺ cell with an appropriate CD4⁺ cell by the method of the subject invention; and (c) comparing the ability of the antibody-containing sample to inhibit the fusion of the CD4⁺ cell with the HIV-1 envelope glycoprotein⁺ cell so determined with that of an antibody-containing sample obtained from an HIV-1 infected subject having an HIV-1 infection at a known stage or having a known clinical prognosis, so as to determine the stage or clinical prognosis of the HIV-1 infection in the HIV-1-infected subject.

As used herein, an "HIV-infected subject" means a subject having at least one of his own cells invaded by HIV-1. In the preferred embodiment, the subject is a human.

The subject invention further provides a method for determining the efficacy of an anti-HIV-1 vaccination in a vaccinated, non-HIV-1-infected subject which comprises: (a) obtaining an antibody-containing sample from the vaccinated, non-HIV-1-infected subject; (b) quantitatively determining the ability of the antibody-containing sample so obtained to inhibit the fusion of an HIV-1 envelope glycoprotein⁺ cell with an appropriate CD4⁺ cell by the method of the subject invention; and (c) comparing the ability of the antibody-containing sample to inhibit the fusion of the CD4⁺ cell with the HIV-1 envelope glycoprotein⁺ cell so determined with that of an antibody-containing sample obtained from a vaccinated, non-HIV-1-infected subject for whom the anti-HIV-1 vaccination has a known efficacy, so as to determine the efficacy of the anti-HIV-1 vaccination in the vaccinated, non-HIV-1-infected subject.

As used herein, "anti-HIV-1 vaccination" means the administration to a subject of a vaccine intended to elicit the production of antibodies by the vaccinated subject which are capable of specifically binding to epitopes present on an HIV-1 surface envelope glycoprotein. Vaccines in general are well known to those skilled in the art, and comprise an antigen, e.g., a protein, and an adjuvant.

As used herein, the "efficacy of an anti-HIV-1 vaccination" means the degree to which the vaccination or successive vaccinations (i.e., immunization) causes the titre of HIV-1-neutralizing antibodies in the vaccinated subject to increase. In other words, the higher the efficacy of an anti-HIV-1 vaccination, the higher the titre of HIV-1-neutralizing antibodies in the vaccinated subject.

As used herein, a "non-HIV-1-infected subject" means a subject not having any of his own cells invaded by HIV-1. In the preferred embodiment, the subject is a human.

The subject invention further provides a kit for determining whether an agent is capable of specifically inhibiting the fusion of an HIV-1 envelope glycoprotein⁺ cell with an appropriate CD4⁺ cell which comprises, in separate compartments: (a) a suitable amount of an appropriate CD4⁺ cell whose cell membrane is labeled with a first dye; (b) a suitable amount of an HIV-1 envelope glycoprotein⁺ cell whose cell membrane is labeled with a second dye, the HIV-1 envelope glycoprotein⁺ cell being capable of fusing with the CD4⁺ cell of (a) under suitable conditions in the absence of the agent, and the first and second dyes permitting resonance energy transfer therebetween only when juxtaposed within the same membrane; (c) a suitable amount of a first control cell whose cell membrane is labeled with the first dye; and (d) a suitable amount of a second control cell whose cell membrane is labeled with the second dye, the second control cell being capable of non-HIV-1 envelope glycoprotein-mediated fusion with the first control cell of (c) under suitable conditions in the absence of the agent.

The kit of the subject invention may further comprise additional buffers. Furthermore, the cells may either be dried or suspended in liquid or gel.

The suitable amounts of cells are amounts which would permit one skilled in the art to determine, without undue experimentation, whether an agent is capable of specifically inhibiting the fusion of a CD4⁺ cell with an HIV-1 envelope glycoprotein⁺ cell. Such amounts may be readily determined according to methods well known to those skilled in the art.

In one embodiment, the first dye is a rhodamine moiety-containing molecule and the second dye is a fluorescein moiety-containing molecule.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

In one embodiment, the CD4⁺ cell is a CD4⁺ HeLa cell. In another embodiment of the subject invention, the HIV-1 envelope glycoprotein⁺ cell is an HIV-1$_{LAI}$ gp120/gp41⁺ HeLa cell. In a separate embodiment, the CD4⁺ cell is a PM1 cell and the HIV-1 envelope glycoprotein⁺-cell is an HIV-1$_{JR-FL}$ gp120/gp41 HeLa cell. In a further embodiment, the CD4⁺ cell is a primary human T lymphocyte. In a still further embodiment, the CD4⁺ cell is a primary human macrophage.

The subject invention further provides a kit for determining whether an agent is capable of inhibiting the fusion of a CD4⁺ cell with an HIV-1 envelope glycoprotein⁺ cell which comprises, in separate compartments: (a) a suitable amount of a CD4⁺ cell whose cell membrane is labeled with a first dye; and (b) a suitable amount of an HIV-1 envelope glycoprotein⁺ cell whose cell membrane is labeled with a second dye, the HIV-1 envelope glycoprotein⁺ cell being capable of fusing with the CD4⁺ cell of (a) under suitable conditions in the absence of the agent, and the first and second dyes permitting resonance energy transfer therebetween only when juxtaposed within the same membrane.

The kit of the subject invention may further comprise additional buffers. Furthermore, the cells may either be dried or suspended in a liquid or gel carrier.

The suitable amounts of cells are amounts which would permit one skilled in the art to determine, without undue experimentation, whether an agent is capable of inhibiting the fusion of a CD4⁺ cell with an HIV-1 envelope glycoprotein⁺ cell. Such amounts may be readily determined according to methods well known to those skilled in the art.

In one embodiment, the first dye is a rhodamine moiety-containing molecule and the second dye is a fluorescein moiety-containing molecule.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

In one embodiment, the CD4+ cell is a CD4+ HeLa cell. In another embodiment of the subject invention, the HIV-1 envelope glycoprotein+ cell is an HIV-1$_{LAI}$ gp120/gp41+ HeLa cell. In a separate embodiment, the CD4+ cell is a PM1 cell and the HIV-1 envelope glycoprotein+-cell is an HIV-1$_{JR-FL}$ gp120/gp41 HeLa cell. In a further embodiment, the CD4+ cell is a primary human T lymphocyte. In a still further embodiment, the CD4+ cell is a primary human macrophage.

The subject invention further provides a method for determining whether an HIV-1 isolate is syncytium-inducing which comprises: (a) obtaining a sample of an HIV-1 isolate envelope glycoprotein+ cell whose cell membrane is labeled with a first dye; (b) contacting a suitable amount of the sample with a suitable amount of a CD4+ cell under conditions which would permit the fusion of the CD4+ cell with a syncytium-inducing HIV-1 strain envelope glycoprotein+ cell, the cell membrane of the CD4+ cell being labeled with a second dye which permits resonance energy transfer between the first dye only when the first and second dyes are juxtaposed within the same membrane; (c) determining the percent resonance energy transfer value of the resulting sample after a suitable period of time; and (d) comparing the percent resonance energy transfer value so determined with a known standard, so as to determine whether the HIV-1 isolate is syncytium-inducing.

As used herein, "syncytium-inducing" means capable of causing the formation of syncytia (multi-nucleated cells resulting from HIV-1 envelope glycoprotein-mediated cell fusion) when contacted with a plurality of CD4+ cells under suitable conditions.

Obtaining a sample of an HIV-1 isolate envelope glycoprotein cells may be performed according to methods well known to those skilled in the art.

HIV-1 isolate envelope glycoprotein+ cells may be obtained from blood or any other bodily fluid known to contain HIV-1 isolate envelope glycoprotein+ cells in HIV-infected subjects. Alternatively, HIV-1 isolate envelope glycoprotein+ cells may be obtained by culturing cells in vitro with blood or other bodily fluids containing the HIV-1 isolate or HIV-1 isolate-infected cells, and recovering the HIV-1 isolate envelope glycoprotein+ cells produced thereby.

The suitable amounts of sample and CD4+ cell may be determined according to methods well known to those skilled in the art.

In one embodiment, the first dye is a rhodamine moiety-containing molecule and the second dye is a fluorescein moiety-containing molecule.

In the preferred embodiment, the rhodamine moiety-containing molecule is octadecyl rhodamine B chloride and the fluorescein moiety-containing molecule is fluorescein octadecyl ester.

In another embodiment, the first dye is a fluorescein moiety-containing molecule and the second dye is a rhodamine moiety-containing molecule.

In one embodiment, the CD4+ cell is a CD4+ HeLa cell. In another embodiment, the CD4+ cell is a PM1 cell. In a further embodiment, the CD4+ cell is a primary human T lymphocyte. In a still further embodiment, the CD4+ cell is a primary human macrophage.

The subject invention further provides a method for determining the stage of an HIV-1 infection in an HIV-1-infected subject which comprises determining by the method of the subject invention whether the HIV-1 isolate with which the HIV-1-infected subject is infected is syncytium-inducing, so as to thereby determine the stage of the HIV-1 infection in the HIV-1-infected subject.

Finally, the subject invention provides a method for quantitatively measuring the fusion of an HIV-1 envelope glycoprotein+ cell with an appropriate CD4+ which comprises: (a) contacting a sample of the appropriate CD4+ cell with the HIV-1 envelope glycoprotein+ cell under conditions permitting fusion therebetween, the cell membranes of the CD4+ cell and the HIV-1 envelope glycoprotein+ cell being labeled with a first dye and a second dye, respectively, which first and second dyes permit resonance energy transfer therebetween only when juxtaposed within the same membrane; (b) determining the percent resonance energy transfer value of the resulting sample after a suitable period of time; and (c) comparing the percent resonance energy transfer value so determined with a known standard, so as to quantitatively measure the fusion of the CD4+ cell with the HIV-1 envelope glycoprotein+ cell.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

First Series of Experiments

A Background

The RET-based fusion assay of the subject invention measures fusion between cells which express the HIV-1 envelope glycoprotein (gp120/gp41) and cells which express CD4. Such cell-cell fusion may lead to the production of multinucleated cells or syncytia. Molecules which block HIV-1 attachment or fusion to host cells also block syncytia formation. Syncytia assays have been used in many laboratories to detect virus or anti-virus molecules, and typically have a visual readout. In the development of the assay, permanent cell lines which stably express gp120/gp41 or CD4 were used.

The resonance energy transfer technique has been used in a variety of studies of membrane fusion including the fusion of nucleated cells induced by viruses or polyethylene glycol. However, it has not previously been used to study HIV-1 envelope glycoprotein-mediated membrane fusion. The technique involves labeling one fusion partner (e.g. a gp120/gp41-expressing cell line) with a fluorescent dye such as octadecyl fluorescein (F18) and the other fusion partner (e.g. a CD4-expressing cell line) with a dye such as octadecyl rhodamine (R18). The dyes are chosen such that the emission spectrum of one (F18) overlaps the excitation spectrum of the second (R18). When the cells fuse, the F18 and R18 associate together closely enough that stimulation of F18 results in resonance energy transfer to R18 and emission at the R18 emission wavelengths. The octadecyl versions of the fluors spontaneously insert into the plasma membranes of cells using the labeling protocol described below.

B Cells Tested (1) A Chinese Hamster Ovary (CHO) cell line which expresses HIV-1$_{IIIB}$ gp120/gp41 (160G7) was mixed with a human T lymphocyte cell line which expresses CD4 (C8166). CD4+ cells are commercially available. 160G7 cells may be obtained at the MRC AIDS Directed Program (United Kingdom). C8166 cells may be obtained at the MRC AIDS Directed Program (United Kingdom) and the NIH AIDS Research and Reference Reagent Program (Bethesda, Md.). It was previously demonstrated that 160G7 cells and C8166 cells fuse to form multinucleated syncytia. This assay is a syncytium assay which requires visual counting of syncytia with the aid of a low power microscope. This assay is suitable for analyzing blocking agents such as CD4-based molecules and neutralizing antibodies directed against gp120 and gp41.

(2) Human epithelial carcinoma (HeLa) cells which express HIV-$1_{LAI}$ gp120/gp41 (HeLa-env) and HeLa cells which express CD4 (HeLa-CD4$^+$) were also used. HeLa-CD4$^+$ cells may be obtained at the MRC AIDS Directed Program (United Kingdom) and the NIH AIDS Research and Reference Reagent Program (Bethesda, Md.). HeLa-env$^+$ cells express much higher levels of gp120/gp41 than do 160G7 cells, as demonstrated by the ability to easily detect gp120 on the surface of HeLa-env$^+$ cells but not 160G7 cells by flow cytometry using an anti-gp120 antibody. Visual analysis demonstrates that HeLa-env$^+$ cells fuse readily with C8166 and HeLa-CD4$^+$ cells to form syncytia.

HeLa-env$^+$ cells may be obtained, for example, by transfecting HeLa cells with an env-encoding plasmid, such as pMA243, using the calcium phosphate precipitation method and subsequent selection of transfectants with 2 $\mu$M methotrexate. The plasmid pMA243 is designed to express the HIV-$1_{LAI}$ genes env, tat, rev and vpu, in addition to the selectable marker DHFR*, with all genes under the control of the HIV-1 LTR (Dragic, T., et al., J. Virol. 66:4794–4802 (1992)). DHFR* is a mutant dihydrofolate reductase gene that demonstrates a reduced affinity for methotrexate. In pMA243, the DHFR* gene is expressed from the mRNA spliced transcript that normally encodes the HIV-1 nef gene which is deleted in this vector. The HIV-1-encoded tat and rev genes are required for high level expression of the env gene. The plasmid pMA243 also encodes an ampicillin resistance marker and bacterial origin of replication.

C Cuvette Assay Method

The cell labeling conditions were modified from those used in a previous study where RET was used to monitor polyethylene glycol-induced cell fusion (Wanda, P. E., and Smith, J. D., J. Histochem. Cytochem. 30:1297 (1982)). F18 (fluorescein octadecyl ester; Molecular Probes Eugene, Oreg. Catalog No. F3857) or R18 (octadecyl rhodamine B, chloride salt; Molecular Probes, Catalog No. 0246) were dissolved in ethanol at 5–10 mg/ml and diluted approximately 1000-fold into the appropriate growth medium. The exact concentration in the medium was adjusted to bring the OD to 0.34 at 506 nm (F18) or 1.04 at 565 nm (R18). Monolayers of cells were incubated with the appropriate medium overnight, then washed and counted. 100,000 cells of each type were mixed together in wells of a 24-well tissue culture plate. At intervals after mixing, the cells were removed with EDTA, washed and placed in a fluorometer cuvette. Fluorescence was measured at three sets of excitation and emission wavelengths (see table 1 below) using a Perkin-Elmer LS50 fluorometer.

TABLE 1

| Excitation wavelength | Emission wavelength | measurement obtained |
|---|---|---|
| 450 nm | 530 nm | Total F18 fluorescence |
| 557 nm | 590 nm | Total R18 fluorescence |
| 450 nm | 590 nm | RET* |

*The calculation of RET requires first subtracting the fluorescence due to direct F18 and R18 fluorescence following excitation at 450 and emission at 590. The fluorescence measurements are determined by measuring the fluorescence of cells labeled with each dye separately.

The RET value, calculated as described above, is divided by the total R18 fluorescence to give a % RET value. The results of initial experiments indicate that RET can be measured using both cell combinations listed above. A greater signal was produced when the envelope glycoprotein-expressing cells were F18-labeled and the CD4-expressing cells were R18 labeled than when the envelope glycoprotein-expressing cells were R18-labeled and the CD4-expressing cells were F18 labeled.

D Results of Time Course RET Studies and Experiments With Control Cell Lines, Using the Cuvette Assay Method Time course experiments were performed with the HeLa-env$^+$+HeLa-CD4$^+$ combination (FIG. 1). A control cell line, HeLa-$\Delta$env$^+$, was used. HeLa-$\Delta$env$^+$ cells express HIV-1 envelope glycoprotein, with a 400 base pair deletion in the gp120-encoding region of the env gene. These cells do not fuse with CD4$^+$ human cells.

The results demonstrate that fusion can be measured by the RET assay at 2 hours, but not at 1 hour, consistent with previous studies of HIV-1 envelope-mediated cell fusion using fluorescence microscopy. At 4 hours, massive cell fusion was evident by visual inspection of the culture, and this time point yielded reproducible RET values in several experiments. In other experiments, the combination of 160G7 cells with C8166 cells gave a reproducible maximum RET value at about 4 hours but with lower values than those obtained using HeLa-env$^+$ and HeLa-CD4$^+$ (data not shown). Presumably, this difference results from the much greater level of gp120/gp41 expression on HeLa-env$^+$ cells as compared with 160G7 cells.

A number of control experiments were performed using combinations of cells which, based on previous studies, are known not to fuse. These combinations included HeLa cells combined with HeLa-CD4$^+$ cells, or HeLa-env$^+$ cells combined with CHO-CD4 or the human glioma cell line U87.MG-CD4. CHO-CD4 cells, like other non-primate cells, do not fuse with cells expressing HIV-1 gp120/gp41. U87.MG-CD4 cells are one of the few CD4$^+$ human cell lines which do not fuse with HIV-1 envelope glycoprotein-expressing cells. RET values obtained with these combinations of cells (data not shown) were in general similar to those using the control HeLa-$\Delta$env$^+$+HeLa-CD4$^+$ (FIG. 1).

Figure 2:
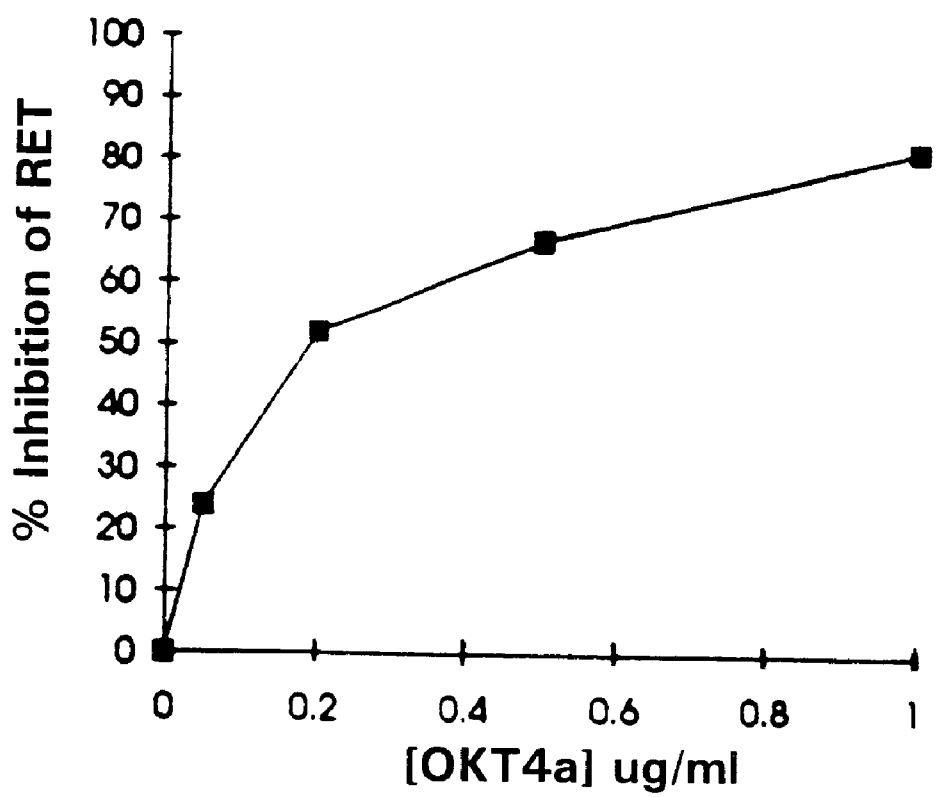
FIG. 2 Blocking of fusion between HeLa-env$^+$ cells and HeLa-CD4$^+$ cells by OKT4a, measured using RET.
Figure 3:
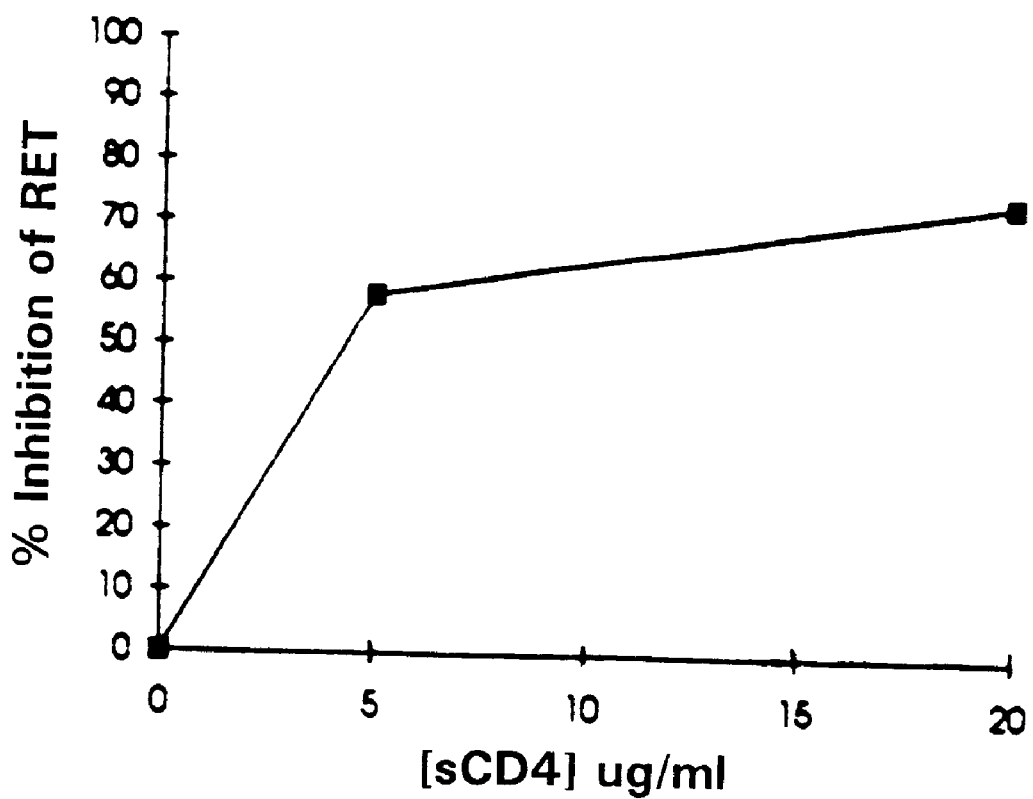
FIG. 3 Blocking of fusion between 160G7 cells and C8166 cells by sCD4, measured using RET.

E Results of RET Experiments With Blocking Agents Using the Cuvette Assay Method It was next determined whether sCD4 (which interacts with gp120/gp41$^+$ cells) or the murine MAb OXT4a (which interacts with CD4$^+$ cells) could block RET (FIGS. 2 and 3). Both these molecules are known to inhibit HIV-1 infection and syncytium formation. The percent blocking was calculated as t RET at each concentration of blocking agent divided by e RET in the absence of blocking agent at 4 hours.

As shown in FIGS. 2 and 3, both sCD4 and OKT4a block fusion as measured by RET. The concentrations of these agents required for 50% inhibition are similar to those determined using other assays. For example. the IC$_{50}$ for sCD4 inhibition of fusion between 160G7 an C8166 was approximately 4 $\mu$g/ml measured using the RET assay, as compared with 5.5 $\mu$g/ml measured by a visual syncytium assay (i.e., an assay for measuring the inhibition of syncytium formation, wherein the syncytia are quantitated visually using a low-power microscope) using the same combination of cells. In summary, these results demonstrate that the RET method can be used to measure HIV-1 envelope-mediated cell fusion in a rapid and reproducible fashion. When compared with data from the more conventional visual syncytium assay, the results are in excellent agreement.

F Control Blocking Experiment With IKT4 Using Cuvette Assay Method

Control experiments were performed to examine inhibition of % RET by OKT4. OKT4 is a mouse monoclonal antibody that binds CD4 but does not inhibit the CD4-gp120 interaction, HIV-1 infection, or HIV-induced cell fusion. Using the cuvette method and the HeLa-env$^+$+HeLa-CD4$^+$ combination, OKT4 gave 0% inhibition of RET at 0.2 μg/ml or 2.0 μg/ml, compared with 65% inhibition by OKT4a at 0.2 μg/ml in the same experiment. These results demonstrate that inhibition of HIV-1 envelope-mediated membrane fusion as measured by RET is specific for agents that block HIV-1 infection and HIV-induced cell fusion.

G Automation of the RET Assay Using the Plate Reader Assay

A fluorescence plate reader was used to analyze the RET assay. This method has the advantage of reducing the manipulations required, notably the need to remove cells for measurement of fluorescence in a cuvette. The plate reader measures fluorescence of cells directly in a multi-well tissue culture plate. Moreover, the speed of assay readout is dramatically increased (by approximately 100-fold). The Millipore "Cytofluor" was used in this experiment. This is a dedicated plate reader which has been used in a variety of different cell-based fluorescence assays and is suitable for use with a range of plate formats including 24-well and 96-well tissue culture plates. The Cytofluor also has the major advantages of speed and compatibility with IBM software analysis programs.

The results indicate that the assay can be readily performed in 24 or 96 well tissue culture plates using the fluorescence plate reader.

In one embodiment, when performing the assay on a routine basis, two types of measurements are done. In the first, RET is measured at a single time point following mixing of labeled cells and a candidate blocking agent. In the second, the assay is adapted to measure changes in the rate of cell fusion in the presence or absence of blocking agents. One of the advantages of the RET assay is that it measures fusion in real time and thus is amenable to kinetic analysis.

For example, a method of using the plate reader assay and measuring RET at a single time point is provided below. In this assay a 96-well flat bottom tissue culture plate is used. The method is a modification of the cuvette method described above.

Example of a single time-point plate reader assay method:
1. Prepare dyes:
   R18: 10 mg/ml in 100! EtOH (for HeLa-CD4$^+$ cells)
   F18: 5 mg/ml in 100% EtOH (for HeLa-env$^+$ cells)
2. Add dyes to appropriate concentrations, in cell culture medium containing 10% fetal calf serum, as determined by absorbance measurements:
   F18$^+$ medium: 0.34 at 506 nm
   R18$^+$ medium: 0.52 at 565 nm
3. Add medium+dye to the appropriate cells as indicated above, then incubate overnight to stain cells.
4. Wash cells and count.

5. Plate out 20,000 cells of each line/well, some wells having one or other cell line separately, other wells with both cell lines, and other wells with various concentrations of antibodies or other inhibitory agents added in addition to both cell lines.

6. 4 hours later, remove the media and wash all of the wells three times with PBS (the cells remain adherent in the wells). Add 200 μl PBS to each well. Read fluorescence in the wells using the Millipore Cytofluor plate reader with filter combinations listed below:
   F18: excitation 450 nm emission 530 nm (X)
   R18: excitation 530 nm emission 590 nm (Y)
   F18+R18: excitation 450 nm emission 590 nm (Z)

The emission values, X, Y and Z (as indicated above) are recorded for each cell combination:
   A) HeLa-env$^+$+HeLa-CD4$^+$
   B) HeLa-env$^+$ alone
   C) HeLa-CD4$^+$ alone For example, the F18 reading for HeLa-env$^+$ cells alone is given by $B_x$.

Then % RET is calculated using this formula:

$$\% RET = \frac{A_Z - (A_X \cdot B_Z / B_X) - (A_Y \cdot C_Z / C_Y)}{A_Y} \cdot 100$$

Figure 4:
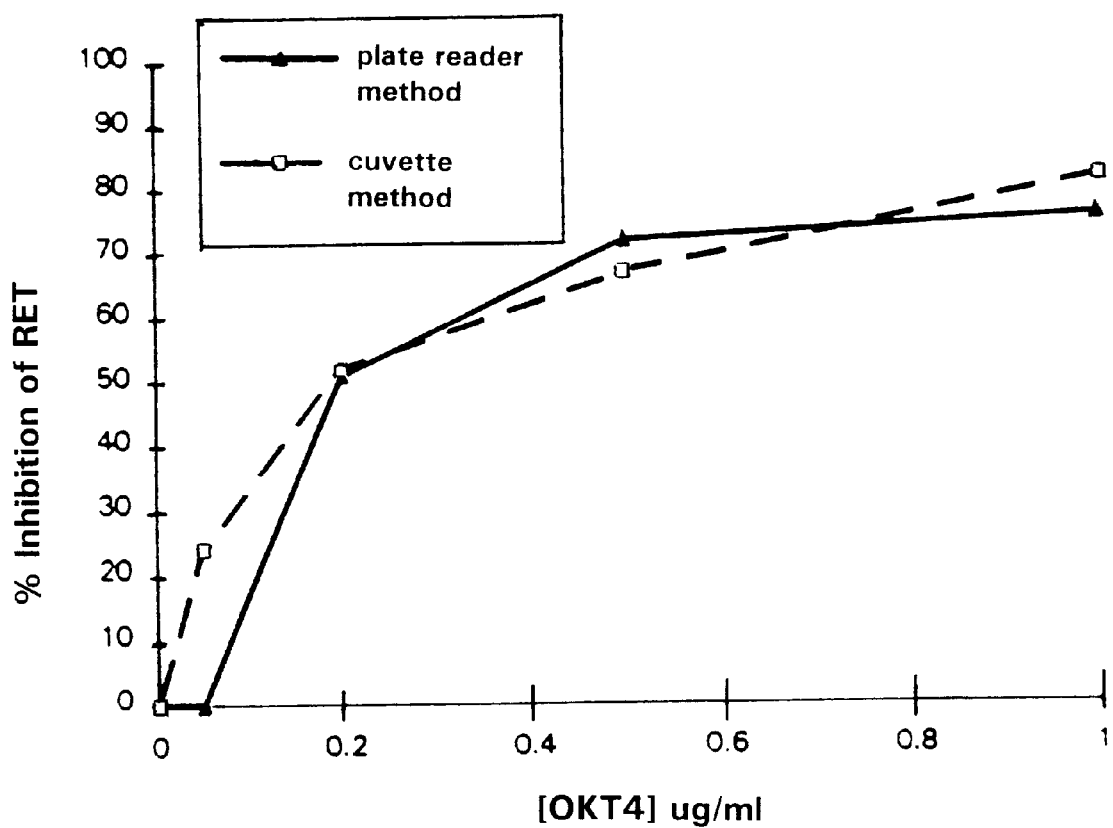
FIG. 4 A comparative analysis of results of blocking experiments by two methods using OKT4a to inhibit the fusion of HeLa-env$^+$ and HeLa-CD4$^+$ cells.

Similar results were obtained in experiments comparing inhibition of % RET using the cuvette method and the plate reader method. For example, FIG. 4 illustrates the inhibition of fusion between HeLa-env$^+$ and HeLa-CD4$^+$ cells by the monoclonal anti-CD4 antibody, OKT4a, measured as a reduction in % RET determined by both methods at 4 hours after mixing the cells.

Second Series of Experiments

As discussed in the first series of experiments, the properties of laboratory-adapted strains of HIV-1 differ from those of primary isolates of the virus. While the former infect continuous T lymphoblastoid cell lines or other human cell lines engineered to express human CD4, the latter are often macrophage-tropic and usually infect only primary macrophage cultures. Macrophage-tropic isolates of HIV-1 are particularly important because they are usually the strains which mediate transmission from individual to individual, whether this transmission is by sexual, parenteral or vertical routes (Zhu, T., et al., Science 261:1179(1993); van't Wout, A. B., et al. J. Clin. Invest., 94:2060 (1994)).

In the first series of experiments, examples were presented where resonance energy transfer (RET) was used to measure cell fusion mediated by laboratory-adapted strains of the virus (e.g. HIV-1$_{LAI}$). In this case, HeLa cells stably expressing the HIV-1$_{LAI}$ envelope glycoprotein were mixed with HeLa cells stably expressing human CD4 and the level of cell fusion measured by RET determinations at intervals following mixing.

In the first series of experiments, applicants referred to the stable HeLa cell line expressing the envelope glycoprotein of HIV-1$_{LAI}$ as HeLa-env$^+$. Applicants will now refer to these cells as HeLa-env$_{LAI}{}^+$ to distinguish them from the HeLa-env$_{JR-FL}{}^+$ cells described below.

Since the properties of macrophage-tropic strains of HIV-1 differ from those of laboratory-adapted strains, applicants have now developed a RET assay to measure membrane fusion mediated by the envelope glycoprotein of a macrophage-tropic HIV-1 isolate. Applicants believe this assay would have particular advantages for identifying agents which inhibit fusion mediated by macrophage tropic strains of the virus. Such agents might differ from those identified using the HeLa-env$_{LAI}$ envelope glycoprotein RET assay. In the drug screening context, agents which inhibit fusion mediated by a macrophage-tropic isolate envelope glycoprotein might be more valuable as lead compounds in the development of drugs for the treatment of HIV-1 infection.

As described in more detail below, applicants have constructed a HeLa cell line (HeLa-env$_{JR-FL}^+$) which stably expresses the envelope glycoprotein from the macrophage tropic strain HIV-1$_{JR-FL}$ (Koyanagi, Y. et al., Science 236:819(1987)). RET measurements indicated that HeLa-env$_{JR-FL}^+$ cells do not fuse with HeLa-CD4$^+$ cells or the CD4$^+$ T lymphoblastoid cell line C8166. Applicants then tested HeLa-env$_{JR-FL}^+$ cells for ability to fuse with three cell lines that are reportedly susceptible to infection by macrophage tropic HIV-1 isolates. These include the T-cell/B-cell hybrid cell line CEM×174 (Stefano, K. A., et al., J. Virol. 67:6707 (1993)), the monocytic leukemia cell line THP-1 (Meylan, P. R. A. et al., Virology 193:256 (1993)), and the cell line PM1 which was recently derived from the Hut78 T lymphoblastoid cell line (Lusso, P., et al., J. Virol. 69:3712 (1995)). RET measurements show that HeLa-env$_{JR-FL}^+$ cells fuse with PM1 cells, but not with CEM×174 or THP-1. Fusion of HeLa-env$_{JR-FL}^+$ cells with PM1 cells was inhibited by agents such as the antibody OTK4A, which inhibits HIV-1 attachment. This indicates that fusion measured in this RET assay is specifically induced by the interaction of the HIV-1$_{JR-FL}$ envelope glycoprotein with CD4. We have modified the RET assay to make it suitable for detecting agents which inhibit fusion mediated by HIV-1$_{JR-FL}$. This assay uses the semi-automated microplate format described as one of two format options in the original application.

Construction of an Expression Vector Encoding HIV-1$_{JR-FL}$ gp120/gp41

The HIV-1$_{JR-FL}$ envelope glycoprotein (gp120/gp41) was expressed using the vector pMA243$_{JR-FL}$. This is identical to the vector pMA243 used to express HIV-1$_{LAI}$ gp120/gp41, except that the HIV-1$_{LAI}$ gp120/gp41 coding sequences were excised from pMA243 and replaced by the HIV-1$_{JR-FL}$ coding sequences. pMA243 is described in Dragic, T., et al., J. Virol. 66:4794 (1992) as well as previously on page 41. pMA243 has been deposited with the ATCC as described previously on page 19.

The Detailed Method for Constructing pMA243$_{JR-FL}$ was as Follows

The HIV-1$_{JR-FL}$ envelope sequence was amplified by PCR from the plasmid vector pUCFL112–1 (kindly provided by Dr. I. S. Y. Chen, U.C.L.A., CA) and subcloned into the vector pMA243. Splicing by overlap Extension (SOEing) was used to create the HIV-1$_{JR-FL}$ gp160-dhfr* gene segment. First, the HIV-1$_{JR-FL}$ gp160 sequence was amplified from pUCFL112-1 using primers 1 and 2. Primer 1 (5'-ATT-CAG-AAG-AGT-CGC-CAG-AGT-AGA-AAA-GTT-GTG-GGT-CAC-3') annealed to the 5' end of gp160 gene (5' to the KpnI site) while primer 2 (5'-GAT-GGC-ACC-AAG-CTT-ATC-GAT-CTT-ATA-GCA-AAG-CCC-TTT-CCA-AGC-3') included the antisense strand of the env-dhfr* intergenic region fused to the complement of the 3' end of the HIV-1$_{JR-FL}$ gene. Next, the dhfr* sequence was amplified from pMA243 using primers 3 and 4. Primer 3 (5'-GAT-CGA-TAA-GCT-TGG-TGC-CAT-CAT-GGT-TCG-ACC-ATT-GAA-CTG--3') included the sense strand of the env-dhfr* intergenic region fused to the 5' end of the dhfr* gene while primer 4 (5'-ATG-AGC-CTT-GTG-TGT-GGT-AG-3') annealed within the 3'-LTR region. The two PCR products were pooled, excess primer removed and a second round of PCR was performed in the presence of primers 1 and 4. The final PCR product consisted of the HIV-1$_{JR-FL}$ envelope gene fused to the dhfr* gene. Lastly, the KpnI fragment of pMA243 (encompassing the HIV-1$_{LAI}$ envelope and dhfr* genes) was excised and replaced with the HIV-1$_{JR-FL}$ gp160-dhfr* gene segment. To verify that no mutations were introduced by the cloning procedure the KpnI fragment was sequenced using the dideoxy method. The resultant plasmid has been designated pMA243$_{JR-FL}$.

Transfection of pMA243$_{JR-FL}$ into HeLa Cells

The cell line HeLa-env-$_{JR-FL}^+$ was made by introducing the plasmid pMA243$_{JR-FL}$ into HeLa cells using the lipofectin procedure (Gibco BRL, Grand Island, N.Y.), following the manufacturer's protocol. Transfectants were selected in 2 μM methotrexate and cloned twice by limiting dilution. Expression levels of gp120 in HeLa-env$_{JR-FL}^+$ were determined by flow cytometry and by an enzyme linked immunosorbent assay for detecting gp120 shed into the culture supernatant.

RET Assay

Staining of cells was similar to that described in the first series of experiments with minor modifications. The modified procedure works effectively with all cell combinations as described below. Octadecyl rhodamine B, chlorine salt (R18) and fluorescein octadecyl ester (F18) (Molecular Probes, Eugene, Oreg.) are dissolved in 100% EtOH to final concentrations of 10 mg/ml and 5 mg/ml, respectively. R18 is then diluted 1:2000 in the appropriate complete tissue culture medium (without selection) and the dye concentration adjusted such that the OD at 565 nm is 0.52±5%. F18 is diluted 1:1000 in complete culture medium and adjusted such that the OD at 506 nm is 0.34±5%. Medium containing F18 is placed on monolayers of the appropriate envelope-expressing cell line (HeLa-env$_{LAI}^+$ or HeLa-env$_{JR-FL}$). Medium containing R18 is either placed on monolayers of the appropriate CD4-bearing cell in the case of adherent cells (e.g. HeLa-CD4$^+$) or added to an equal volume of medium containing suspension cells (e.g. PM1 cells). Adherent cells are stained when they are approximately 60–80% confluent. Suspension cells are stained at a concentration of 0.25–0.5×10$^6$/ml. Cells are then incubated overnight in the fluorescent dye-containing culture media.

Following staining, adherent cells are removed from culture flasks by treatment with 0.5 mM EDTA and washed several times in culture media containing 10% FBS. Suspension cells are washed by several cycles of centrifugation. 20,000 envelope-expressing cells are plated with an equal number of CD4 expressing cells per well of a 96 well plate and incubated for 4 hours at 37 C. Where both cell lines are adherent, flat-bottomed well plates are used. Round-bottomed well plates are used where the CD4-expressing cell is a suspension cell line (e.g. PM1 cells). Controls include wells containing each cell line alone. Following three washes in PBS (with low speed centrifugation between washes for the suspension cells), the fluorescence is read in a Millipore Cytofluor plate reader using the filter combinations previously described on page 48.

% RET Calculation

The emission values, X, Y and Z are recorded for each cell combination:

A) HeLa or HIV-1 envelope glycoprotein-expressing HeLa cells+CD4-expressing cells.

B) HeLa or HIV-1 envelope glycoprotein-expressing HeLa cells alone.

C) CD4-expressing cells alone.

Percent RET is then calculated using the formula previously described on page 49.

Experimental Results

% RET results obtained using this assay with various cell combination are given in Table 2. As shown in Table 2, HeLa-env$_{LAI}^+$ cells fuse readily with HeLa-CD4$^+$ cells (% RET value >5). Similarly, HeLa-env$_{LAI}$ cells fuse readily with the CD4$^+$ T lymphoblastoid cell line C8166. In both cases fusion is inhibited to background levels (% RET values <1) by the antibody OTK4A (Ortho Diagnostic Systems, Raritan, N.J.). OKT4A is an anti-CD4 antibody which is known to block the binding of gp120 to CD4, the attachment step of viral entry and an essential prelude to HIV-1 envelope-mediated cell fusion. HeLa-env$_{LAI}^+$ cells do not fuse with chinese hamster ovary cells expressing CD4 (CHO-CD4$^+$), since non-primate cells appear to lack accessory molecules that are required for HIV-1 envelope-mediated cell fusion.

TABLE 2

RET measurements obtained using various combinations of cells and the inhibitory antibody OKT4A (0.3 µg/ml).

| F18 labeled cells | R18 labeled cells | Inhibitor | % RET |
| --- | --- | --- | --- |
| HeLa-env$_{LAI}^+$ | HeLa-CD4$^+$ | none | 7.3 |
| HeLa-env$_{LAI}^+$ | HeLa-CD4$^+$ | OKT4A | 0.4 |
| HeLa | HeLa-CD4$^+$ | none | 0.7 |
| HeLa-env$_{LAI}^+$ | C8166 | none | 13 |
| HeLa-env$_{LAI}^+$ | C8166 | OKT4A | 0.6 |
| HeLa | C8166 | none | 0.5 |
| HeLa-env$_{LAI}^+$ | CHO-CD4$^+$ | none | 0 |
| HeLa-env$_{JR-FL}^+$ | HeLa-CD4$^+$ | none | 0.8 |
| HeLa-env$_{JR-FL}^+$ | C8166 | none | 0 |
| HeLa-env$_{JR-FL}^+$ | CEMx174 | none | 0 |
| HeLa-env$_{JR-FL}^+$ | THP-1 | none | 0 |
| HeLa-env$_{JR-FL}^+$ | PM1 | none | 7.5 |
| HeLa-env$_{JR-FL}^+$ | PM1 | OKT4A | 0.7 |
| HeLa | PM1 | none | 0.3 |

As shown in Table 2, HeLa-env$_{JR-FL}^+$ cells do not fuse with HeLa-CD4$^+$ or C8166 cells as indicated by the background levels of % RET (% RET <1). In this regard, the HeLa-env$_{JR-FL}^+$ cells mimic HIV-1$_{JR-FL}$ which is macrophage tropic. Like other macrophage-tropic HIV-1 isolates, HIV-1$_{JR-FL}$ generally does not fuse with or infect T lymphocyte cell lines or other CD4$^+$ cell lines (O'Brien, W. A. et al., Nature 348:69 (1990)).

Figure 5:
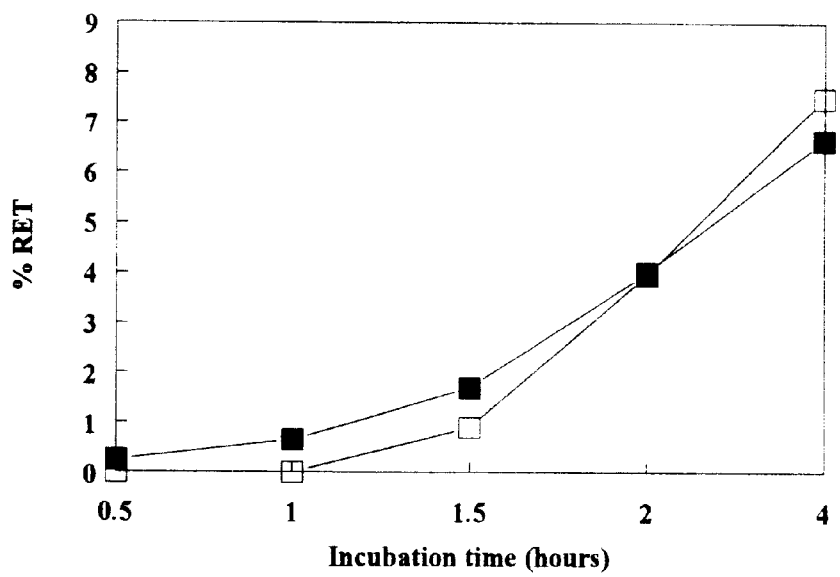
FIG. 5 RET time course analysis. The time course of fusion between HeLa-env$_{LAI}{}^+$ and HeLa-CD4$^+$ cells (open boxes) or HeLa-env$_{JR-FL}{}^+$ and PM1 cells (closed boxes) was measured using the RET assay at various intervals after mixing the cells.

Next, applicants tested several cell lines which have been reported to be infectable by macrophage-tropic strains of HIV-1 as described above. Applicants found that HeLa-env$_{JR-FL}^+$ cells did not fuse with CEMx174 or THP-1 cells in the RET assay (Table 2). Applicants also tested fusion between HeLa-env$_{JR-FL}^+$ cells and the PM1 cell line. These cells were obtained from M. Norcross (FDA, Bethesda, Md.) and M. Crowley (NIH, Bethesda, Md.). As shown in Table 2, HeLa-env$_{JR-FL}^+$ cells and PM1 cells did fuse as determined by % RET measurements. The time course of fusion between HeLa-env$_{JR-FL}^+$ cells and PM1 cells, measured using the RET assay, was similar to that seen with the HeLa-env$_{LAI}^+$ and HeLa-CD4$^+$ cell combination (FIG. 5). Note that the results using HeLa-env$_{LAI}^+$ and HeLa-CD4$^+$ cells are similar to, but not identical with, those presented in FIG. 1. The minor differences may result from the use of the plate reader assay method in FIG. 5 rather than the cuvette assay method in FIG. 1.

Figure 6:
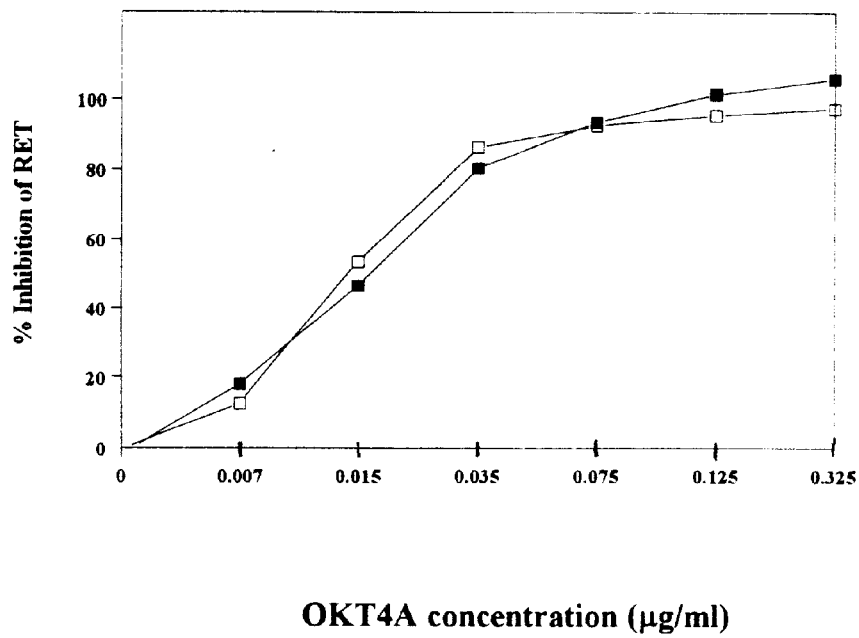
FIG. 6 Inhibition of RET using the anti-attachment monoclonal antibody OKT4A. % RET resulting from the fusion of HeLa-env$_{LAI}{}^+$ and HeLa-CD4$^+$ cells (open boxes) or HeLa-env$_{JR-FL}{}^+$ and PM1 cells (closed boxes) was measured in the presence and absence of various concentrations of OKT4A. Percent inhibition of RET at each concentration of OTK4A was calculated from this formula.

The specificity of fusion between HeLa-env$_{JR-FL}^+$ and PM1 cells measured using the RET assay is supported by the lack of fusion (background % RET measurements) obtained when HeLa-env$_{JR-FL}$ cells were mixed with other CD4$^+$ cells (Table 2 and above). Moreover, only background levels of % RET were found when PM-1 cells and HeLa cells were mixed in the assay (Table 2). Finally, fusion between PM-1 cells and HeLa-env$_{JR-FL}^+$ cells, measured by the RET assay, was as sensitive to inhibition by OKT4A as was fusion between HeLa-env$_{LAI}^+$ cells and HeLa-CD4$^+$ cells (FIG. 6). RET was completely inhibited to background levels by 0.3 µg/ml OKT4A (Table 2). No inhibition of RET was seen using the same concentration of the antibody OTK4 (Ortho Diagnostic Systems), which does not inhibit HIV-1 attachment (not shown).

Third Series of Experiments

Inibition of HIV-1 envelope glycoprotein-mediated membrane fusion in the RET assay by anti-PM1 hybridoma supernatants The RET assay described in this application is useful for screening antibodies capable of inhibiting HIV-1 envelope glycoprotein-mediated membrane fusion. Hybridomas against PM1 cells were generated and the supernatants from these hybridomas were screened in the RET assay to identify hybridomas which secret antibodies capable of inhibiting fusion between HeLa-env$_{JR-FL}$ and PM1 cells. The culture supernatants from hybridomas PA-3, PA-5, PA-6 and PA-7 inhibited fusion between HeLa-env$_{JR-FL}$ and PM1 cells in the RET assay, and also inhibited fusion between HeLa-env$_{LAI}$ cells and certain CD4$^+$ target cells (Table 3). HIV-1$_{LAI}$ envelope glycoprotein-mediated membrane fusion with PM-1 and HUT-78 was inhibited by all of the mAb secreted from these hybridoma cell lines. Whereas, fusion between HeLa-env$_{LAI}$ and CEM was inhibited by PA-3 and PA-5 but less so by PA-6 or PA-7. The fusion between HeLa-env$_{LAI}$ and C8166 or Sup-T1 cells was inhibited minimally or not at all by these mAb.

TABLE 3

Inhibition of HIV-1 envelope glycoprotein mediated cell fusion by novel mAb.

| Envelope expressing cells | CD4$^+$ cell | % RET | % Inhibition of RET by novel mAb | | | |
| --- | --- | --- | --- | --- | --- | --- |
| | | | PA-3 | PA-5 | PA-6 | PA-7 |
| HeLa-env$_{JR-FL}$ | PM-1 | 16.3 | 85.3 | 96.3 | 92 | 67 |
| HeLa-env$_{LAI}$ | PM-1 | 12.4 | 89.7 | 100 | 81 | 69 |
| HeLa-env$_{LAI}$ | HUT-78 | 10.9 | 51.3 | 60.3 | 55.7 | 52.7 |
| HeLa-env$_{LAI}$ | CEM | 9.5 | 71.8 | 68 | 33 | 21 |
| HeLa-env$_{LAI}$ | HeLa-CD4 | 11.4 | 0 | 0 | 7.7 | 0 |
| HeLa-env$_{LAI}$ | SUP-T1 | 19.8 | 2.5 | 0 | 18 | 11 |
| HeLa-env$_{LAI}$ | C8166 | 15.4 | 9.7 | 22 | 22.3 | 13 |

Effect of β-chemokines on HIV-1 envelope glycoprotein-mediated membrane fusion analysed by the RET assay The RET assay was developed further to analyze fusion between cells expressing the HIV-1 envelope glycoprotein and primary CD4$^+$ cells. CD4$^+$ target cells (mitogen-activated primary human CD4$^+$ lymphocytes, primary human macrophages or PM1 cells) were labeled with octadecyl rhodamine (Molecular Probes, Eugene, Oreg.), and Hela-env$_{JR-FL}$ cells, HeLa-env$_{LAI}$ cells (or control HeLa cells, not shown) were labeled with octadecyl fluorescein (Molecular Probes), overnight at 37° C. Equal numbers of labeled target cells and env-expressing cells were mixed in 96-well plates and β-chemokines (or the CD4 MAb OKT4a) were added at the final concentrations (ng/ml) indicated in parentheses in the first column of Table 4.

Fluorescence emission values were determined 4 h after cell mixing. RET and percentage inhibition of RET were calculated as described above. In this experiment, HeLa-env$_{JR-FL}$ fused with CD4$^+$ normal human T-lymphocytes (% RET=6.0) and macrophages (% RET=4.3) as well as PM1 cells (% RET=11.5). HeLa-env$_{LAI}$ also fused with CD4$^+$ normal human T-lymphocytes (% RET =10.5) and PM1 cells (% RET=10.5) but not with macrophages (% RET=1.2, similar to % RET using HeLa cells in place of HeLa-env cells).

TABLE 4

Inhibition of membrane fusion by β-chemokines

|  | % Inhibition of RET | |
|---|---|---|
|  | HeLa-env$_{JR-FL}$ | HeLa-env$_{LAI}$ |
| a) PM1 cells | | |
| no chemokines | 0 | 0 |
| +R/Mα/Mβ (80/400/100) | 99 | 5 |
| +RANTES (80) | 92 | 0 |
| +MIP-1α (400) | 61 | 0 |
| +MIP-1β (100) | 87 | 7 |
| +MCP-1 (100) | 1 | 2 |
| +MCP-2 (100) | 28 | 7 |
| +MCP-3 (100) | 2 | 1 |
| b) LW5 CD4$^+$ cells | | |
| no chemokines | 0 | 0 |
| +R/Mα/Mβ (106/533/133) | 61 | 0 |
| +RANTES (106) | 35 | 5 |
| +MIP-1α (533) | 28 | 0 |
| +MIP-1β (133) | 56 | 8 |
| +OKT4A (3 ug/ml) | 100 | 100 |
| c) EU2 CD4$^+$ cells | | |
| no chemokines | * | 0 |
| +R/Mα/Mβ (320/1600/400) | * | 0 |
| +RANTES (320) | * | 0 |
| +MIP-1α (1600) | * | 0 |
| +MIP-1β (400) | * | 0 |
| d) Macrophages | | |
| no chemokines | 0 | * |
| +R/Mα/Mβ (80/400/100) | 54 | * |
| +RANTES (80) | 20 | * |
| +MIP-1α (400) | 15 | * |
| +MIP-1β(100) | 37 | * |
| +MCP-1 (100) | 0 | * |
| +MCP-2 (100) | 28 | * |
| +MCP-3 (100) | 18 | * |

*No detectable fusion

As shown in Table 4, RANTES, MIP-1β (and to a lesser extent, MIP-1α) strongly inhibited membrane fusion of HeLa-env$_{JR-FL}$ cells with PM1 cells, whereas fusion between PM1 cells and HeLa-env$_{LAI}$ cells was insensitive to these β-chemokines (Table 4a). Similar results were obtained with primary CD4$^+$ T-cells from a normal laboratory worker (LW5, Table 4b), although higher concentrations of β-chemokines were required to inhibit membrane fusion in the primary cells than in PM1 cells. Thus, the actions of the β-chemokines are not restricted to the PM1 cell line. In marked contrast to LW5's cells, CD4$^+$ T-cells from an exposed but uninfected individual (EU2) did not fuse with HeLa-env$_{JR-FL}$ cells (% RET=0.1), whereas they could clearly fuse with HeLa-env$_{LAI}$ cells (% RET=4.1) in a β-chemokine-resistant manner (Table 4c). Fusion between HeLa-env$_{JR-FL}$ and primary macrophages was inhibited only weakly by the β-chemokines, while HeLa-env$_{LAI}$ did not fuse with primary macrophages (Table 4d). The RET assay demonstrates that β-chemokines interfere with env-mediated membrane fusion. It also establishes that envelope glycoproteins from a primary, NSI strain cannot fuse with CD4$^+$ T-cells from an EU individual, providing a critical clue to how these cells may resist HIV-1 infection in vitro, and perhaps in vivo.

What is claimed is:

1. A method for determining whether an agent is capable of specifically inhibiting (A) the fusion of a macrophage-tropic primary isolate of HIV-1 to a CD4$^+$ cell susceptible to infection by a macrophage-tropic HIV-1 or (B) the fusion of a T cell-tropic isolate of HIV-1 to a cell susceptible to infection by a T cell tropic HIV-1, but not both, which comprises:

(a) contacting (i) a first appropriate CD4$^+$ cell, which is labeled with a first dye, with (ii) a cell expressing the HIV-1 envelope glycoprotein of the macrophage-tropic primary isolate of HIV-1 on its surface, which is labeled with a second dye, in the presence of an excess of the agent under conditions which would normally permit the fusion of the CD4$^+$ cell to the cell expressing the HIV-1 envelope glycoprotein on its surface in the absence of the agent, the first and second dyes being selected so as to allow resonance energy transfer between the dyes;

(b) exposing the result of step (a) to conditions which would result in resonance energy transfer if fusion has occurred; and (c) determining whether there is a reduction of resonance energy transfer, when compared with the resonance energy transfer in the absence of the agent;

(d) contacting (i) a second appropriate CD4$^+$ cell, which is labeled with a first dye, with (ii) a cell expressing the HIV-1 envelope glycoprotein of a T cell-tropic isolate of HIV-1 on its surface, which is labeled with a second dye, in the presence of an excess of the agent under conditions which would normally permit the fusion of the CD4$^+$ cell to the cell expressing the HIV-1 envelope glycoprotein on its surface in the absence of the agent, the first and second dyes being selected so as to allow resonance energy transfer between the dyes;

(e) exposing the result of step (d) to conditions which would result in resonance energy transfer if fusion has occurred; and (f) determining whether there is a reduction of resonance energy transfer, when compared with the resonance energy transfer in the absence of the agent, wherein a decrease in transfer in step (c) but not step (f) indicates that the agent is capable of specifically inhibiting fusion of the macrophage-tropic primary isolate of HIV-1 to CD4$^+$ cells and a decrease in transfer in step (f) but not step (c) indicates that the agent is capable of specifically inhibiting the fusion of a T cell-tropic isolate of HIV-1 to the CD4$^+$ cells.

2. The method of claim 1, wherein the first appropriate CD4$^+$ cell is a PM1 cell, a primary human T lymphocyte, or a primary human macrophage.

3. The method of claim 1, wherein the second appropriate CD4$^+$ cell is a HeLa-CD4 cell, a primary human T lymphocyte, a human T cell line, PM1 cell, or a C8166 cell.

4. The method of claim 1, wherein in step (a) the cell expressing the HIV-1 envelope glycoprotein of the macrophage-tropic primary isolate is an HIV-1$_{JR-FL}$ gp120/gp41 HeLa cell.

5. The method of claim 1, wherein in step (d) the cell expressing the HIV-1 envelope glycoprotein of the T-cell-tropic of HIV-1 is an HIV-1$_{LAI}$ gp120/gp41 HeLa cell.

6. The method of claim 1 wherein the agent is not previously known.

7. The method of claim 1, wherein the first dye is a rhodamine moiety-containing molecule and the second dye is a fluorescein moiety-containing molecule.

8. The method of claim 7, wherein the rhodamine moiety-containing molecule is octadecyl rhodamine B chloride and the fluorescein moiety-containing molecule is fluorescein octadecyl ester.

9. The method of claim 1, wherein the first dye is a fluorescein moiety-containing molecule and the second dye is a rhodamine moiety-containing molecule.

* * * * *